United States Patent
Aptekar et al.

(10) Patent No.: US 11,977,550 B1
(45) Date of Patent: May 7, 2024

(54) SYSTEM AND METHOD FOR GENERATING A SYNTHETIC LONGITUDINAL DATASET FROM AN ORIGINAL DATASET

(71) Applicant: MEDIDATA SOLUTIONS, INC., New York, NY (US)

(72) Inventors: Jacob Aptekar, Oakland, CA (US); Mandis S. Beigi, White Plains, NY (US); Pierre-Louis Bourlon, New York, NY (US); Jason Mezey, New York, NY (US); Afrah Shafquat, Jericho, NY (US); Jimeng Sun, Las Vegas, NV (US)

(73) Assignee: MEDIDATA SOLUTIONS, INC., New York, NY (US)

( * ) Notice: Subject to any disclaimer, the term of this patent is extended or adjusted under 35 U.S.C. 154(b) by 0 days.

(21) Appl. No.: 18/299,577

(22) Filed: Apr. 12, 2023

(51) Int. Cl.
  *G06F 16/2457* (2019.01)
(52) U.S. Cl.
  CPC .................. *G06F 16/2457* (2019.01)
(58) Field of Classification Search
  CPC .................................. G06F 16/2457
  See application file for complete search history.

(56) References Cited

U.S. PATENT DOCUMENTS

| | | | |
|---|---|---|---|
| 2012/0030165 A1 | 2/2012 | Guirguis et al. | |
| 2018/0025303 A1* | 1/2018 | Janz | G16H 50/20 705/2 |
| 2019/0156061 A1 | 5/2019 | Chakraborty et al. | |
| 2021/0133621 A1 | 5/2021 | Ravizza et al. | |
| 2022/0067202 A1 | 3/2022 | Nedelec et al. | |
| 2023/0060848 A1 | 3/2023 | Beigi et al. | |

FOREIGN PATENT DOCUMENTS

CN 108111294 A 6/2018

OTHER PUBLICATIONS

El Emam et al., "Optimizing the synthesis of clinical trial data using sequential trees," Journal of the American Medical Informatics Association, 28(1), 2021. [version submitted retrieved from https://academic.oup.com/jamia/article/28/1/3/5981525 (11 pages)].

(Continued)

*Primary Examiner* — Baoquoc N To
(74) *Attorney, Agent, or Firm* — STEPTOE & JOHNSON LLP; Carl B. Wischhusen

(57) ABSTRACT

Generating a synthetic longitudinal dataset includes identifying subsequence patterns in records defining event sequences for patients. Feature vectors are determined, each characterizing a corresponding one of the records, based on the subsequence patterns. The feature vectors are embedded in a lower dimension space. A seed record is iteratively selected from among the records and in each iteration: subsequence patterns are identified in a subset of the records. Instances of subsequence patterns in the seed record are replaced with instances of similar subsequence patterns identified in the subset of the records to form a modified seed record. The iterations are repeated until all of the records have been selected as the seed record. The modified seed records are combined to form the synthetic dataset.

26 Claims, 16 Drawing Sheets

(56) References Cited

OTHER PUBLICATIONS

El Emam et al., "Anonymizing health data," O'Reilly Press Cambridge, 2014, pp. 1-44.
European Medicines Agency, Workshop Report "Data anonymisation—a key enabler for clinical data sharing," Dec. 2018. [version submitted retrieved from https://www.ema.europa.eu/en/documents/report/report-data-anonymisation-key-enabler-clinical-data-sharing_en.pdf (32 pages)].
Franconi et al. "Community Innovation Survey: comparable dissemination", EUROSTAT Methodologies and Working papers, 2009 edition, pp. 11-23.
Hall, Correlation-based Feature Selection for Machine Learning [thesis: The University of Waikato], Apr. 1999 [retrieved Nov. 26, 2021], 198 pgs. Retrieved: https://www.cs.waikato.ac.nz/-ml/publications/1999/99 MH-Thesis.pdf (Year: 1999).
Kasthurirathne et al., "Generative Adversarial Networks for Creating Synthetic Free-Text Medical Data: A Proposal for Collaborative Research and Re-use of Machine Learning Models," Proceedings—AMIA Joint Summits on Translational Science, pp. 335-344, May 2021.
McInnes et al., "UMAP: Uniform Manifold Approximation and Projection for Dimension Reduction", [open-access archive], Sep. 18, 2020 [retrieved Nov. 26, 2021], Cornell University:arXiv, v3, 63 pgs. Retrieved: https://arxiv.org/abs/1802.03426 (Year: 2020).
Park et al., "Data synthesis based on Generative Adversarial Networks," Proceedings of the VLDB Endowment, vol. 11, No. 10, Jul. 2018. [version submitted retrieved from arXiv:1806.03384v5 (16 pages)].
Sivakumar et al. "Synthetic sampling from small datasets: A modified mega-trend diffusion approach using k-nearest neighbors", Knowledge-Based Systems, vol. 236, 2022, pp. 1-12.
Srivastava et al., "VEEGAN: Reducing Mode Collapse in GANs using Implicit Variational Learning," 31st Conference on Neural Information Processing Systems, Nov. 2017. [version submitted retrieved from arXiv:1705.07761v3 (17 pages)].
Torra et al., "Evaluating Fuzzy Clustering Algorithms for Microdata Protection", PSD 2004, LNCS 3050, 2004, pp. 175-186.
Wang et al., "Privacy-preserving high-dimensional data publishing for classification", online: Mar. 3, 2020 [retrieved Jul. 29, 2022], Computers & Security, vol. 93, pp. 1-10. Retrieved: https://www.sciencedirect.com/science/article/pii/S0167404820300705 (Year: 2020).
Xu et al., "Modeling Tabular Data using Conditional GAN," 33rd Conference on Neural Information Processing Systems, Oct. 2019. [version submitted retrieved from arXiv:1907.00503v2 (15 pages)].
Yale et al. "Generation and evaluation of privacy preserving synthetic health data", Neurocomputing, vol. 416, 2020, pp. 244-255.
Zhang, J. et al., "PrivBayes: Private Data Release via Bayesian Networks," ACM Transactions on Database Systems, vol. 42, No. 4, Article 25, 2017, pp. 1-41. [version submitted retrieved from https://dl.acm.org/doi/pdf/10.1145/3134428].
Zhang, Z. et al., "Ensuring electronic medical record simulation through better training, modeling, and evaluation," Journal of the American Medical Informatics Association 27(1): 2019, pp. 99-108. [version submitted retrieved from https://academic.oup.com/jamia/article/27/1/99/5583723].
Zhu et al. "Private-kNN: Practical Differential Privacy for Computer Vision", 2020 IEEE/CVF Conference on Computer Vision and Pattern Recognition (CVPR), 2020, pp. 11851-11859.
Abraham et al., "Advances in Intelligent Systems and Computing: Emerging Technologies in Data Mining and Information Security: Probabilistic Dimension Reduction Method for Privacy Preserving Data Clustering", 2018, Springer, vol. 813, 864 pgs.
Armanious et al., "MedGAN: Medical Image Translation using GANs," Computerized Medical Imaging and Graphics, vol. 79, 2020. [version submitted retrieved from arXiv:1806.06397v2 (16 pages)].
Beaulieu-Jones et al., "Privacy-preserving generative deep neural networks support clinical data sharing," BioRxiv, 2018 [version submitted retrieved from BioRxiv https://doi.org/10.1101/159756 preprint posted Jul. 2017 (16 pages)].
Beaulieu-Jones, Brett K. et al., "Privacy-Preserving Generative Deep Neural Networks Support Clinical Data Sharing," Circulation: Cardiovascular Quality and Outcomes, Jul. 2019.
Bindschaedler et al., "Plausible Deniability for Privacy-Preserving Data Synthesis" (Extended Version) [open access archive]; Aug. 26, 2017 [retrieved Nov. 26, 2021], Cornell University: arXiv, v1, 17 pages. Retrieved: https://arxiv.org/abs/1708.07975v1 (Year. 2017).
Choi et al., "Generating Multi-label Discrete Patient Records using Generative Adversarial Networks," Proceedings of Machine Learning for Healthcare, vol. 68, 2017. [version submitted retrieved from arXiv:1703.06490v3 (20 pages)].
Edge et al., "Design of a Privacy-Preserving Data Platform for Collaboration Against Human Trafficking", Sep. 18, 2020 [retrieved Jul. 29, 2022], Cornell University:arXiv [open-access archive], version v2, pp. 1-19. Retrieved: https://arxiv.org/abs/2005.05688 (Year: 2020).

\* cited by examiner

SYSTEM AND METHOD FOR GENERATING A SYNTHETIC LONGITUDINAL DATASET FROM AN ORIGINAL DATASET

BACKGROUND

Technical Field

The present disclosure generally relates to generating a synthetic longitudinal dataset from an original dataset.

Description of the Related Art

Innovations in health care technology are now originating from the analysis of aggregated patient-level data. Currently, the most important category of such data is electronic health records (EHR), where public and private aggregations of EHR are now being leveraged to prioritize drug development programs, optimize study design, and improve healthcare delivery processes, among many other applications. A closely related but distinct category of patient-level data that are increasingly important for health care technology, are the patient-level data from clinical trials, which are collected through Electronic Data Capture (EDC) technology.

While there are strong parallels between patient-level EHR and EDC, compared to EHR which are collected sporadically from patient driven visits to healthcare providers, EDC are collected for patients who have consented to be part of a controlled experiment. These experiments are designed to make high value inferences (e.g., impact of a drug versus placebo on patient survival for a specific disease under a specific treatment regime). EDC data represents high-dimensional data collected repeatedly for each patient on regular schedules under carefully controlled and regulated processes. EDC patient sample sizes can be in the tens or hundreds compared to thousands for many EHR data sets. For applications such as estimating the power of a clinical trial design, discovering concomitant drug impacts, or identifying patient factors that can impact clinical trial success rates, EDC can have considerably higher value as a data resource than EHR.

While the potential research value of clinical trial data is well appreciated, at present, patient level EDC is largely unavailable for public use. Of the hundreds of thousands of clinical studies run each year throughout the world, only a small percentage has been made broadly available. As with other sensitive data types, the main reason for this limited accessibility is that clinical trial patient level data requires adherence to regulatory, privacy, and technical protection protocols. While anonymization or de-identification techniques could overcome some of these concerns, these techniques do not completely address privacy and confidentiality concerns or the issues of patient consent, because conventional techniques to de-identify and anonymize EDC data do not fully guarantee patient privacy for that type of data.

Conventional techniques, such as Generative Adversarial Networks (GANs), Variational Autoencoders (VAEs) and Natural Language Processing (NLP) techniques, are able to provide privacy control by using deep learning and machine learning to generate synthetic data from the learned distribution. However, these techniques require the large volumes of data afforded by EHR, and do not work well with the smaller datasets of EDC data from clinical trials. Thus, privacy issues, both for subjects and sponsors of clinical trials, still exist.

SUMMARY

Disclosed embodiments provide a method, system, and computer-readable medium to generate high fidelity longitudinal EDC data comprising timed events, while preserving a high level of privacy at subject level. The disclosed techniques balance data fidelity and data privacy by obfuscating the data in a way that preserves its statistical properties while rendering it unidentifiable to unauthorized users. This may allow researchers to more widely access and analyze such data at an earlier stage of clinical trials, which can accelerate the development of new drugs and medical treatments.

Disclosed embodiments combine a low-dimensional embedding of the source data's feature representation to identify a record's nearest neighbors in compressed feature space, with exchanges of similar patterns of events between records. The synthetically generated data is statistically similar to the source data and captures the source's underlying dependencies and patterns of events. The disclosed methods do not memorize or retain records from the original data and do not reveal any specific features from the original data, thereby allowing for the practical use of the disclosed methods given the high privacy bar for patient-level EDC.

In one aspect, the disclosed embodiments provide methods, systems, and computer-readable media to generate a synthetic longitudinal dataset (X'). The method includes identifying subsequence patterns in N records (r) defining event sequences for N patients, resulting in m subsequence patterns, where m and N are integers. The method further includes determining feature vectors (Y'), each characterizing a corresponding one of the records (r), based at least in part on the m subsequence patterns. The method further includes embedding the feature vectors (Y') in a lower dimension space (V) with a dimension y to define locations of the records (r) in the lower dimension space (V), where y is an integer and m>y>0. The method further includes selecting, iteratively, a seed record ($r^s$) from among the records (r). In each iteration the method includes the following: identifying subsequence patterns in a subset of the records (r), the subset being determined based at least in part on the locations of the records (r) in the lower dimension space (V); replacing one or more instances of subsequence patterns in the seed record ($r^s$) with instances of corresponding subsequence patterns identified in the subset of the records (r), based at least in part on a determined distance between the respective instances of subsequence patterns, to form a modified seed record ($r^{s'}$); and repeating the selecting, the identifying, and the replacing until all of the records (r) have been iteratively selected as the seed record ($r^s$). The method further includes combining modified seed records ($r^{s'}$) resulting from the iterations in a synthetic dataset (X').

Embodiments one or more of the following features, alone or in combination.

A dataset (Y) may include event records for the N patients, each event record including a patient identifier, a start date of an event, or a start date of the event and an end date of the event, and one or more attributes of the event. In such a case, the method may further include determining, for each of the N patients, an event sequence ordered by the start date of each event of the event records associated with each respective one of the N patients to produce the N records (r) defining event sequences for N patients.

An original dataset (X) may include a plurality of tables, each table including a subset of the event records for the N patients, in which case the method may further concatenating the tables to form the dataset (Y). Each event record may include an event code identifying a corresponding event associated with each respective event record. The patient identifier of each event record may be uniquely associated with one of the N patients. For at least one of the event records, the event of is one of the following: a clinical procedure, intervention, or treatment; administration of a drug or medication; an occurrence, report, onset, or end of a symptom or condition; an adverse reaction to a drug, medication or treatment; a clinical test, measurement, evaluation, or diagnosis; and an output of a monitoring device; a patient report or complaint. For at least one of the event records, the start date may correspond to a date on which a procedure is performed on a patient identified by the patient identifier. For at least one of the event records, the start date may correspond to a first date on which a patient identified by the patient identifier experiences a symptom and the end date may correspond to a second date on which the patient identified by the patient identifier no longer experiences the symptom. For at least one of the event records, the attributes may include at least one of the following: categorical attributes and numerical attributes.

The m subsequence patterns may include subsequence patterns having a frequency of occurrence greater than a defined threshold. The m subsequence patterns may include m subsequence patterns having the highest frequencies of occurrence, where m is a defined parameter. The feature vectors (Y') may be equal in length. The feature vectors (Y') may include frequencies of occurrence of the m subsequence patterns. The feature vectors (Y') may include binary presence or absence encoding of the m subsequence patterns.

The embedding may be performed using one or more of: t-distributed stochastic neighbor embedding (t-SNE), uniform manifold approximation and projection (UMAP), and principal component analysis (PCA). The subset of records (r) may correspond to the k nearest neighbors of the seed record ($r^s$) in the lower dimension space (V), where k is an integer. The k nearest neighbors of the seed record ($r^s$) may be determined using a Hamming distance or an edit distance. One of the records (r) may be randomly selected as the seed record ($r^s$) in each iteration.

The replacing may be performed only for subsequence patterns for which the determined distance between the respective instances of subsequence patterns is less than a defined distance threshold. The replacing may be performed by replacing the one or more instances of subsequence patterns in the seed record ($r^s$) with instances of corresponding subsequence patterns randomly selected from a group of subsequence patterns having respective distances less than a defined distance threshold. In the replacing, subsequences for which a total number of occurrences in the N event sequences is less than a determined threshold may be excluded.

The method may further include, in each iteration, randomizing a start date of a first event in the seed record ($r^s$). The randomizing may include adding noise sampled from a uniform distribution. The method may further include, in each iteration, randomizing a gap between one or more pairs of the events in the seed record ($r^s$). The randomizing may include adding Gaussian noise.

The method may further include determining, in each of the N event sequences, a conditional probability for each event given that a preceding event has occurred. The method may further include, in each iteration, randomly swapping each event with a respective preceding event when the conditional probability is less than a defined threshold. The method may further include outputting the synthetic dataset (X') to a storage system providing encryption and access controls. In the outputting, the synthetic dataset (X') may be output in at least one of the following formats: CSV, JSON, or binary.

Figure 1:
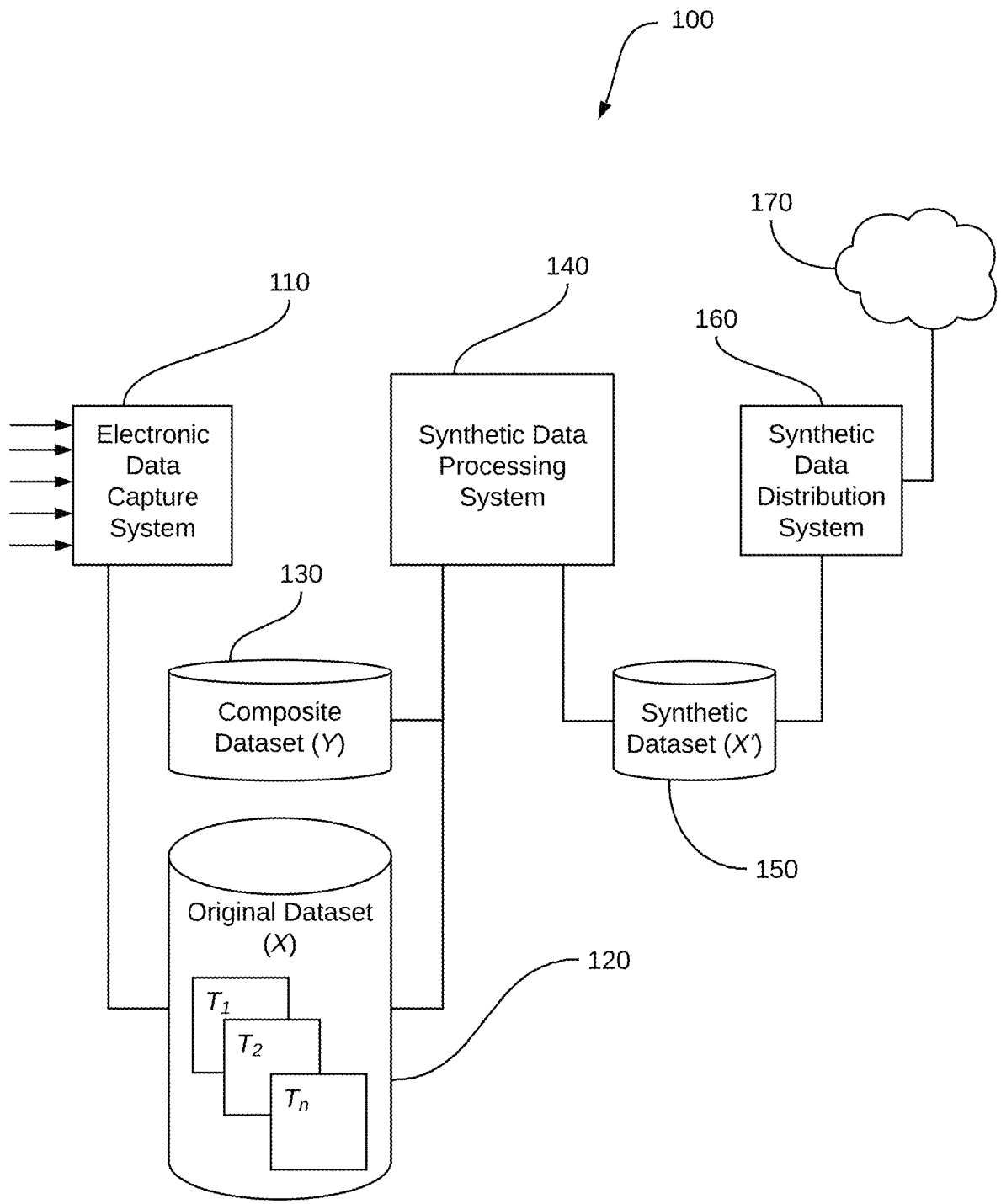
FIG. 1 is a block diagram of a system for generating and distributing a synthetic longitudinal dataset, according to disclosed embodiments.

Where considered appropriate, reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth in order to provide a thorough understanding of embodiments of the invention. However, it will be understood by those of ordinary skill in the art that the embodiments of the present invention may be practiced without these specific details. In other instances, well-known methods, procedures, components, and circuits have not been described in detail so as not to obscure the present invention.

Disclosed embodiments provide a system and method to address the privacy challenges discussed above by generating synthetic longitudinal datasets that still retain high fidelity. The method transforms variable length sequences to fixed length feature vector representations using the frequency of their patterns of events and then uses low-dimensional embedding of the feature vectors to identify a record's neighbors in compressed feature space, thereby identifying a set of similar sequences, i.e., records. The method then finds all the subsequence patterns within the neighborhood of similar sequences and swaps the instances of patterns (i.e., subsequences) that are similar to each other among the different sequences. The method generates high-fidelity, synthetic longitudinal data, while performing enough transformation to the original sequences to maintain privacy.

Maintaining data privacy for clinical trial data is a technical problem, because it requires the development, implementation, and maintenance of complex methodologies and tools to ensure that sensitive patient information is protected and not exposed during data analysis and sharing. While the underlying motivation for ensuring data privacy may stem from ethical, legal, and regulatory concerns, the actual process of achieving data privacy involves addressing a multitude of technical challenges. Addressing data privacy concerns in clinical trial data involves several technical aspects, including:

De-identification and anonymization: These processes involve removing personally identifiable information (PII) from the dataset and ensuring that any remaining information cannot be traced back to individual patients.

Data encryption: Securely storing and transmitting clinical trial data requires the use of robust encryption algorithms to protect the information from unauthorized access or interception.

Differential privacy: This is a framework for guaranteeing privacy and quantifying the privacy risks associated with the release of aggregate data derived from sensitive datasets. Differential privacy techniques introduce controlled changes to the data, making it difficult to infer specific information about individuals while preserving the overall utility of the data for analysis.

Creating a synthetic dataset for clinical trial data is a technical solution to the technical problems discussed above, because it addresses several challenges that are inherent in working with real-world clinical trial data. Synthetic data generation techniques can create datasets that mimic the characteristics of the original data without exposing sensitive information, allowing researchers to work with data while maintaining patient privacy. In some cases, access to clinical trial data can be limited due to various factors, such as proprietary rights, data silos, and strict access controls. Synthetic datasets can help overcome these barriers by generating additional data that shares similar properties with the original data, allowing researchers to develop and validate models without direct access to the real data.

Furthermore, the technical solution involves algorithms and/or rules having specific characteristics which produce synthetic data which is heavily obfuscated, while maintaining the statistical properties of the original dataset. As discussed below, the technical solution is focused on specific improvements in the generation of synthetic datasets through the use of the specific algorithms and/or rules. It is the implementation of the specific algorithms and/or rules, not the mere use of a computer, that improves the existing technological process by providing improved data obfuscation and, hence, improved data privacy. Thus, the technical solution provides a specific approach that improves the relevant technology, as opposed to being directed to an abstract result or effect which merely invokes generic processes and machinery.

In summary, creating synthetic datasets for clinical trial data is a technical solution to a technical problem, because it addresses the specific challenges of data privacy that arise when working with real-world clinical trial data. The technical solution uses specific algorithms and/or rules that render information into a new dataset having a specific set of characteristics (i.e., statistical characteristics similar to those of the original dataset) which is then used and applied to allow researchers to perform analysis of clinical trial data. The algorithms and/or rules described herein go beyond merely organizing existing information into a new form—they produce an entirely new dataset. The use of synthetic data generated in this manner can help overcome the challenges discussed above and enable more effective development, testing, and deployment of data-driven solutions in clinical research.

The following terminology is used herein. "Event" is a term used in a broad sense to refer to an element or item of a sequence of elements or items. An event may be, inter alia, a medical, physiological, or clinical action or occurrence associated with a particular patient, such as: a clinical procedure, intervention, or treatment; the administration of a drug or medication; an occurrence, report, onset, or end of a symptom or condition; an adverse reaction to a drug, medication or treatment; a clinical test, measurement, evaluation, or diagnosis; an output of a monitoring device; a patient report or complaint, etc. "Event group" refers to an unordered or ordered set of events that tend to occur together. "Sequence" refers to an ordered set (typically a set of arbitrary length) of events or event groups. "Sub-sequence" or "subsequence" refers to a set of events or event groups that represent part of a sequence. "Subsequence pattern" refers to a subsequence repeated with a particular frequency in a set or collection of sequences, where the subsequence pattern may be of variable length and may contain gaps (i.e., "wild cards"). "Feature vector" refers to a numerical vector (typically fixed-length) representation of a sequence. An "instance of a subsequence pattern" refers to an occurrence of a subsequence, within a sequence, that matches a subsequence pattern. "Record" or "event record" refers to a sequence of events, in a dataset, associated with a particular patient. The terms "swap" or "swapping," as used herein, may refer to a one-way action, e.g., as in the replacement of a subsequence of a seed record with a corresponding similar (e.g., based on a distance determination) subsequence of another record, or a two-way action, e.g., as in reversing the order of two events in a sequence of events based on their conditional probabilities. "Longitudinal dataset" refers to a set or collection of sequences with associated numerical, temporal, categorical, and/or continuous attributes (e.g., timestamps, parameter values, etc.).

FIG. 1 is a block diagram of a system 100 for generating and distributing a synthetic longitudinal dataset. The system 100 receives clinical trial data, e.g., via an Electronic Data Capture (EDC) system 110, which receives data from a number of data sources, such as clinical sites. The data from the EDC system 110 may be in the form of a dataset, referred to as an "original dataset" 120, designated herein as X. As discussed in further detail below, the original dataset 120 is processed by a synthetic data processing system 140 to produce a synthetic dataset 150, designated herein as X'. The synthetic dataset 150 may be distributed to researchers for analysis, e.g., via a secure data sharing platform, referred to as the synthetic data distribution system 160, which makes the data available via a network 170.

The original dataset 120 may contain a number of variable length sequences, each including either ordered or time-stamped items and itemsets. An item may represent an event which can have a start date and time and optionally an end date and time. Each event may also have additional attributes which can be numerical or categorical. The methods disclosed herein are designed to work on both large and small (ranging from a few hundred to several thousands of subjects) datasets, but are particularly advantageous (compared to the state-of-the-art algorithms) in working with small datasets, such as those that come from clinical trials. Conventional approaches using neural networks, on the other hand, require very large sets of training data.

The original dataset 120 may include a number of tables ($T_1, T_2 \ldots T_n$), with each table containing a subset of the event records for the N patients. For example, clinical trial data may be stored, according to particular standards, as a number of separate tables (e.g., in the CSV format commonly used for spreadsheets), such as a table for subject-level information which contains one row per subject with specific information relating to the respective subject. A number of supplemental tables may provide data regarding adverse events, medications, medical history, possibly including multiple entries for a specific subject.

In embodiments, the tables and records of the original dataset 120 may be combined to form a composite dataset 130, designated herein as Y, which may store data in various data structures, such as rows and columns. The composite dataset Y may have event records for N patients, with each row having a subject ID (i.e., a patient identifier), an event code (identifying a corresponding event associated with the respective event record), an event start date and, optionally, an event end date, and a number of other categorical and numerical values. The event start date of a particular record may correspond to a date on which a procedure is performed on a patient identified by the patient identifier of the particular record. In some cases, the start date of a particular record may correspond to the date on which a patient identified by the patient identifier experiences a particular continuous symptom, and the end date may correspond to a second date on which the patient identified by the patient identifier no longer experiences the particular symptom. The categorical and numerical values may include patient information and demographics (e.g., name, age, gender, country), vital statistics (e.g., height, weight, blood pressure, heart rate, etc.), as well as other types of data.

In disclosed embodiments, a synthetic longitudinal dataset 150 is generated from data received from the EDC system 110. The synthetic longitudinal dataset 150 is designed to mimic the statistical properties of the original dataset 120. This provides for the statistical properties of the original dataset 120 to be preserved, so accurate conclusions can be drawn by researchers, while de-identifying and obfuscating the data to reduce the risk of identifying individual participants and violating their privacy. The statistical properties of the synthetic dataset 150 may be validated against the original dataset 120 to ensure that it closely approximates the original dataset. This validation may be done using a variety of statistical tests, such as regression analysis.

The synthetic dataset may be distributed to researchers for analysis, e.g., via a secure data sharing platform, such as the synthetic data distribution system 160, which may involve setting up a private or public application program interface (API), creating a data repository, data portal, and/or using cloud-based data storage services with appropriate access controls, authentication, and encryption mechanisms. Researchers can use the synthetic dataset 150 to conduct longitudinal analysis with minimal risk of identifying individual participants.

Figure 2:
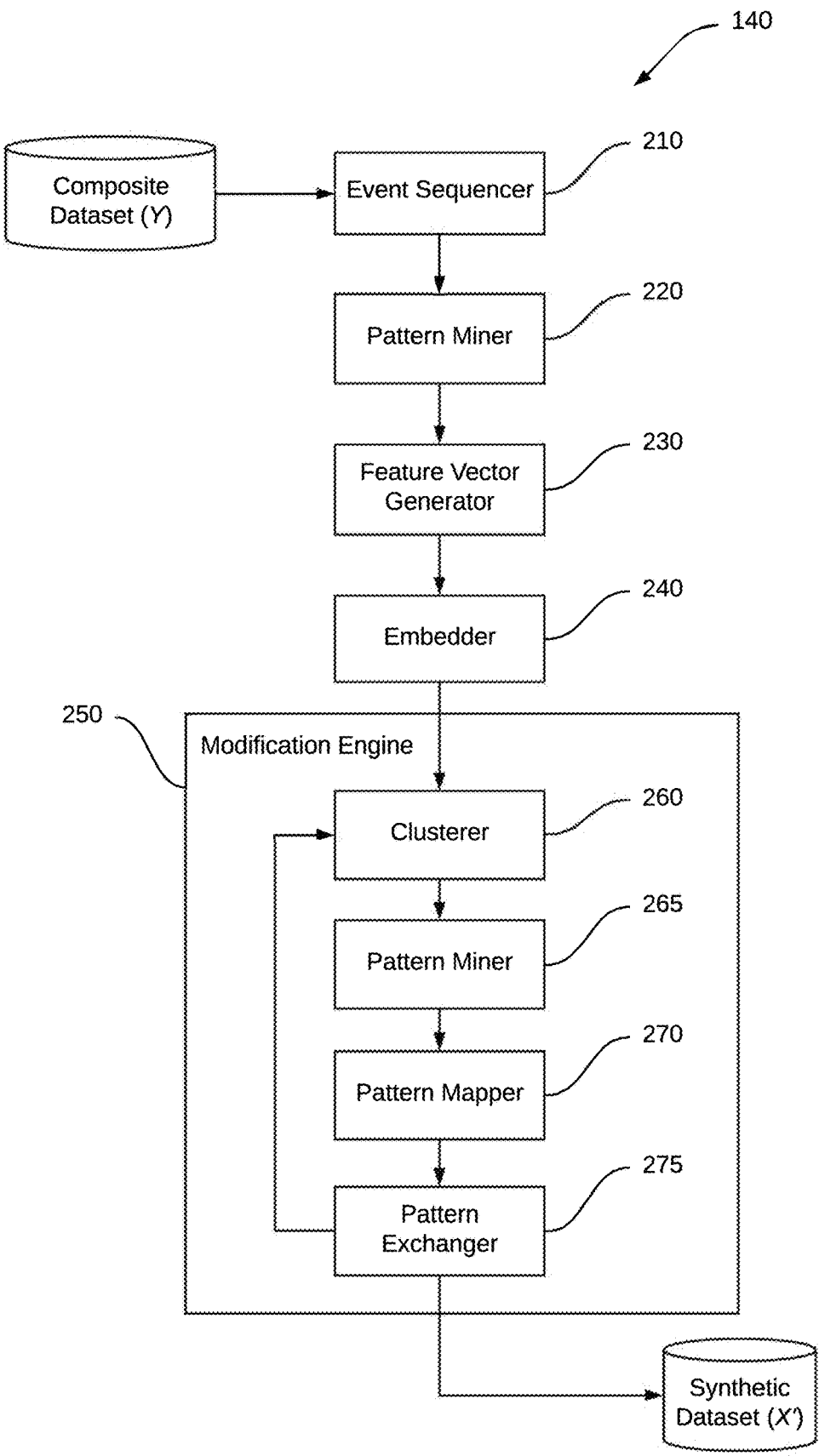
FIG. 2 is a diagram of a synthetic data processing system, according to disclosed embodiments.

FIG. 2 is a diagram of the synthetic data processing system 140. As explained above, an original longitudinal dataset (X) may be received which includes event records for a number, N, of patients (where N is an integer). The tables and records of the original dataset (X) may be combined to form a composite dataset (Y). Each record may include a start date (and, optionally, time) of an event, or both a start date and an end date, and one or more attributes of the event. Based on event information, the event sequencer 210 determines, for each of the N patients, an event sequence ordered by the start date of each event of the event record associated with the respective patient, thereby producing a set of N records (r) defining event sequences for N patients. The event sequences differ in length from patient to patient, because each patient undergoes a particular sequence of events, the length of which is determined by the number of events associated with the respective patient. Some patients may experience, perform, undergo, etc., only a few events, whereas other patients may be associated with a large number of events depending upon their clinical history.

A pattern miner 220 receives input data from the event sequencer 210 and performs analysis to find subsequence patterns, with or without gaps, within all of the sequences. Specifically, this involves identifying subsequence patterns in the N records (r) defining event sequences for N patients, resulting in m subsequence patterns, where m and N are integers. In some implementations, the m subsequence patterns may include all subsequence patterns having a frequency greater than a defined threshold or, alternatively, m patterns having the highest frequency, where m is a defined parameter. Thus, all of the frequent subsequence patterns in the dataset as a whole are identified in the pattern mining (e.g., all subsequence patterns having a frequency over a defined threshold). The patterns may contain gaps or wild cards. For example, a frequent subsequence pattern may be: <event1, event5, event10>.

The feature vector generator 230 generates a set of feature vectors, designated herein as Y', based at least in part on the m subsequence patterns. The feature vectors Y' represent each of the N records (designated here in as r) defining event sequences as a vector which specifies the instances of unique subsequence patterns within each respective event sequence. In some implementations, the feature vectors Y' are equal in length. The feature vectors Y' may be created using frequencies of the subsequence patterns. For example, the feature vectors Y' may be created using frequencies of occurrence of the m subsequence patterns or using binary presence or absence encoding of the m subsequence patterns. Thus, each event sequence, i.e., record (r), has a corresponding feature vector representation, e.g., as a histogram of all the patterns it contains or simply all the items (e.g., events). In some implementations, there is one feature vector generated for each record (r) and all feature vectors have the same length.

The embedder 240 receives the feature vectors Y' and embeds them into a low dimension manifold, i.e., a lower dimension space, designated herein as V, with dimension y, where m>y>0 (with y being an integer) to define locations of the records (r) in the space (V). Each record (r) may be considered to be represented by a point corresponding to a feature vector in the embedded space V. Preferably, y is small, e.g., y=2 or y=3, resulting in a low-dimensional feature space, which makes the subsequent clustering, e.g., k-nearest neighbor clustering, work better. The embedding, in effect, helps determine which records are similar to each other.

In implementations, the embedding may be performed using various methods, such as: t-distributed stochastic neighbor embedding (t-SNE), uniform manifold approximation and projection (UMAP), and principal component analysis (PCA). UMAP is similar to t-SNE, but it assumes that the data are uniformly distributed on a locally connected Riemannian manifold and that the Riemannian metric is locally constant or approximately locally constant. PCA can be used to compute the principal components (i.e., the dimensions in the low-dimensional space) of a set of records and these can be used to perform a change of basis on the data, e.g., by using only the first few principal components and ignoring the rest.

Figure 4:
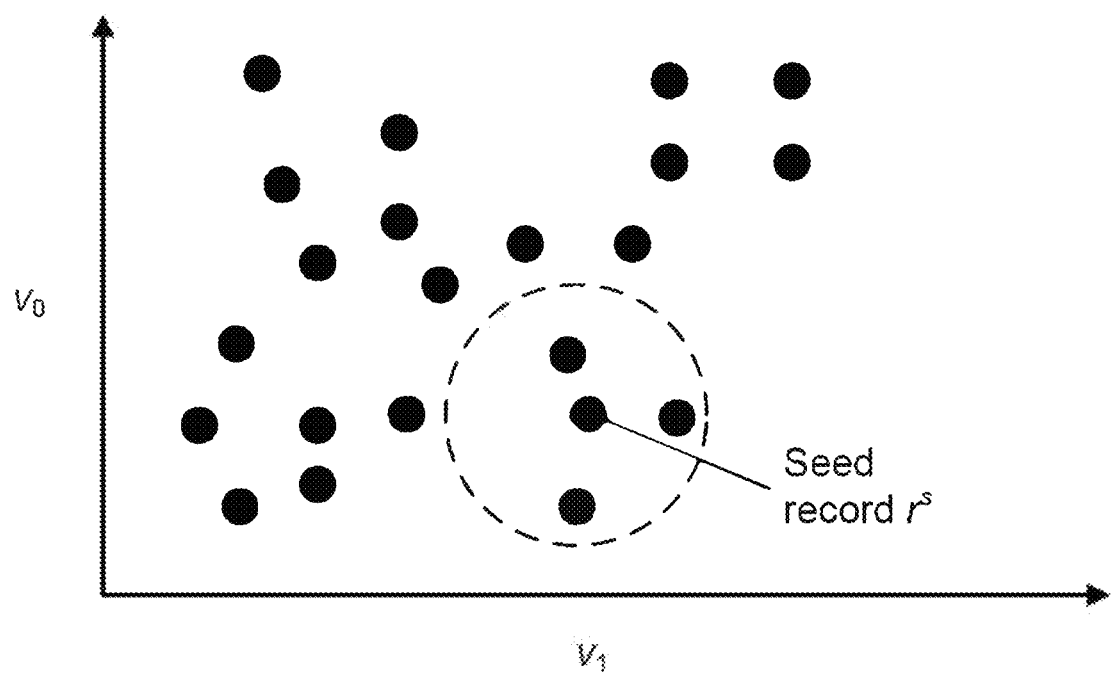
FIG. 4 is a cartesian representation of feature vectors (Y') embedded in a lower dimension space (V).

FIG. 4 is a cartesian representation of the feature vectors (Y') embedded in a lower dimension space (V) with a dimension y=2. Each point (i.e., feature vector location) corresponds to one of the records (r). A point corresponding to the seed record ($r^s$) is surrounded by a cluster of points in space V corresponding to the closest neighboring records (r).

Referring again to FIG. 2, the modification engine 250 receives the records (r) and their embedded representations in the lower dimension space (V) and uses them to produce modified records, i.e., synthetic data records, to produce a synthetic dataset (X'). As discussed in further detail below, this involves iteratively selecting a seed record ($r^s$) from among the records (r) and performing an algorithm to produce a modified seed record ($r^{s\prime}$). These iterations are repeated until all of the records (r) have been iteratively selected as the seed record ($r^s$). The modified seed records ($r^{s\prime}$) resulting from the iterations are combined in a synthetic dataset (X') to be used in place of dataset (Y), e.g., for research purposes.

The modification engine 250 includes a clusterer 260 which defines a subset of the records (r) associated with a particular seed record $r^s$, such as the k nearest neighbors of the seed record $r^s$, using, e.g., a Hamming distance or edit distance. In implementations, one of the records r may be randomly selected as the seed record $r^s$ in each iteration. The value of k may be selected heuristically based on a trade-off between fidelity of the data and difficulty to decode the synthetic dataset, i.e., to deduce records of the original dataset from the synthetic dataset (which, in effect, corresponds to data privacy) and based on the particular application. As k increases, fidelity decreases, but data privacy increases and vice versa.

The modification engine 250 includes a pattern miner 265 to identify subsequence patterns in a selected seed record $r^s$ and its neighboring records r in space V, i.e., based on locations of the embedded feature vectors (Y') which correspond to the records (r). Thus, the pattern miner operates on a subset of the records (r) provided by the clusterer 250. This pattern mining is, in a sense, a localized version of the operation of the pattern miner discussed above (i.e., pattern miner 220), which operated on the dataset (Y) as a whole.

The pattern mapper 270 identifies relationships between corresponding, e.g., similar, patterns. The similarity between instances of the subsequence patterns identified by the pattern miner 265 may be determined based on a calculated distance (e.g., Hamming distance or edit distance) between the subsequences, where "distance" refers to metrics which assess similarity, such as, for example, how many corresponding bit positions differ in equal-length binary representations of the patterns. For example, distances, e.g., Hamming distances, may be determined between the subsequence patterns identified by the pattern miner 265, where a smaller distance is indicative of a greater similarity between the subsequence patterns of the seed record $r^s$ and the selected neighboring records r in space V. In such a case, each subsequence pattern may be matched to corresponding subsequence pattern in the cluster having a distance less than a threshold.

The pattern exchanger 275 then replaces one or more instances of subsequence patterns of the seed record $r^s$ with instances of similar patterns in the neighborhood (i.e., in the cluster) to produce a modified seed record $r^{s\prime}$. A new seed record $r^s$ is determined and operation returns to the clusterer 260. In embodiments, the replacing of instances of subsequence patterns in the seed record $r^s$ with similar subsequence patterns in the neighboring records r in space V is performed based at least in part on the determined distances between the respective instances of the subsequence patterns. In some implementations, swapping is performed only for subsequences having a distance less than a defined distance threshold. In some cases, swapping may be performed by swapping each subsequence of the seed record $r^s$ for a subsequence randomly selected from a group of subsequences having a distance less than a defined distance threshold.

The modified seed records $r^{s\prime}$ produced by the modification engine 250 in the iterations are combined and output as a synthetic dataset X', which may be in the form of a set or collection of event sequences of varying length for N patients. To summarize, these new synthetic records ($r^{s\prime}$) defining event sequences for each patient are generated by going through all the original sequences, i.e., records r, and exchanging their subsequence patterns with subsequence patterns from their respective neighborhood.

The producing of the modified seed records $r^{s\prime}$ may provide for filtering or excluding from the pattern swapping any subsequence patterns for which a total number of occurrences, in the dataset Y as a whole, is less than a determined threshold. The exclusion or filtering eliminates relatively rare events, e.g., a rare adverse reaction or symptom, because such events may make it easier to decode the synthetic dataset, i.e., to deduce records of the original dataset from the synthetic dataset.

Producing the modified seed records $r^{s\prime}$ may include randomizing a start date of a first event in the seed record $r^s$. Such randomizing may include adding noise sampled from a uniform distribution. Producing the modified seed records $r^{s\prime}$ may also include randomizing a gap between each of the events in the seed record $r^s$. Such randomizing may include adding Gaussian noise. This randomization of start date and intervening time between events in a sequence of events makes it more difficult to decode the synthetic dataset, without substantial effect on the fidelity of the data for research uses.

In some implementations, a determination may be made, in each of the N event sequences, of a conditional probability for each event (or event group) given that a preceding event (or event group) has occurred. In such a case, producing the modified seed records $r^{s\prime}$ may include randomly swapping each event with a respective preceding event when the conditional probability with respect to the preceding event is less than a defined threshold.

Figure 3A:
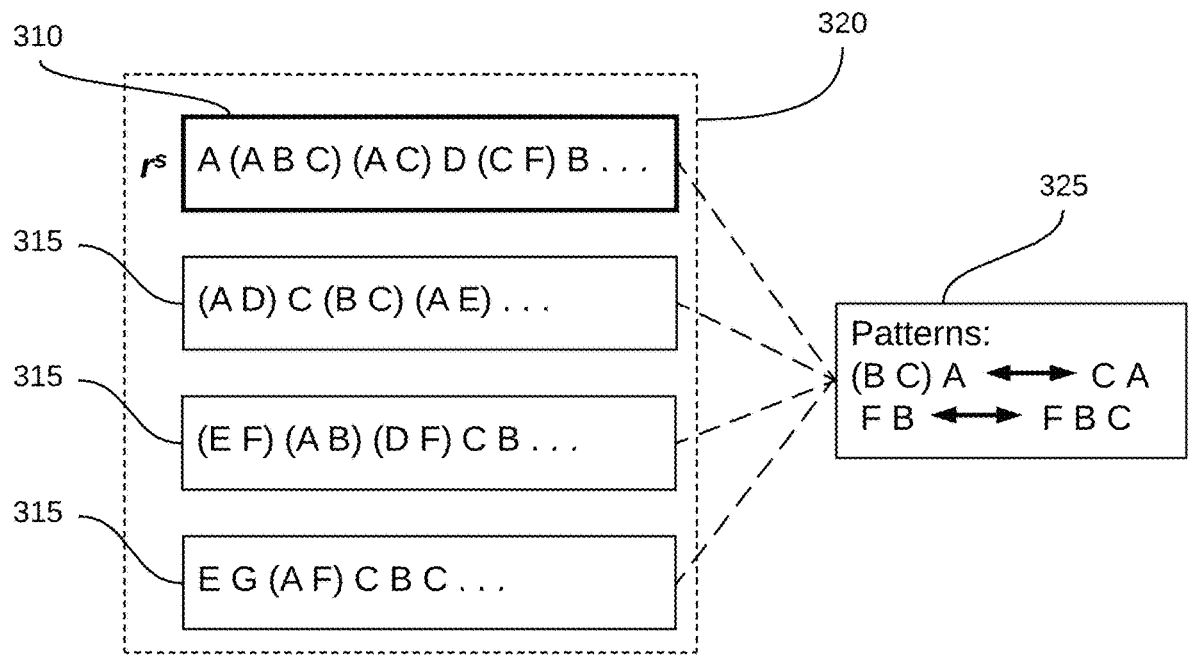
FIGS. 3A and 3B depict an example of instances of subsequence patterns in a seed record being exchanged with corresponding subsequence patterns in records in the same cluster.
Figure 3B:
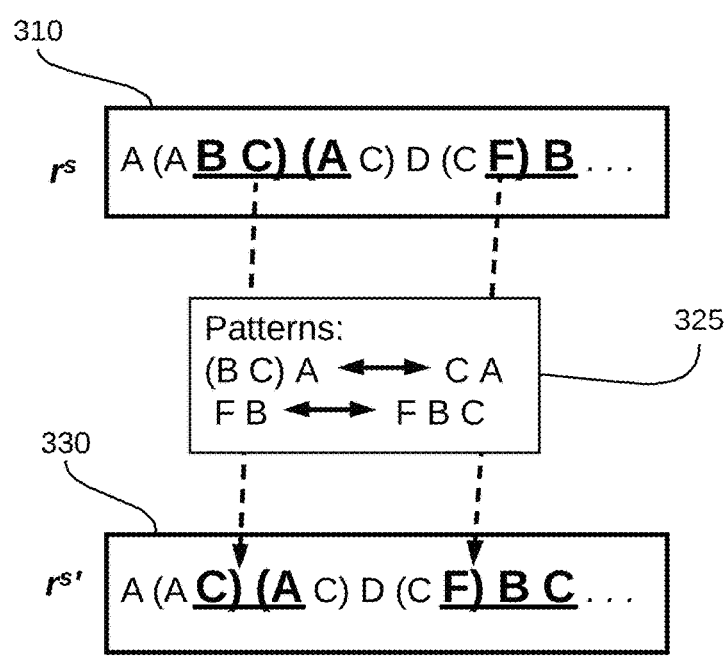

FIGS. 3A and 3B depict an example of instances of subsequence patterns in a seed record 310 being exchanged with corresponding subsequence patterns in records 315 in the same cluster 320. A table 325 is shown which lists examples of the patterns found within the cluster 320 and their similar patterns determined using a distance metric, such as a Hamming distance or edit distance. Itemsets (e.g., event groups) in the seed record 310 or neighboring records 315 include two or more items and are shown within parentheses. The seed record 310, in this example, includes a particular event sequence which includes both events and event groups. Among the events and event groups are two instances of subsequence patterns identified in the cluster 320, i.e., "B C) (A" and "F) B" (see table 325). These subsequences are replaced with the corresponding similar subsequences to produce a modified seed record 330. In embodiments, the subsequence patterns may have gaps and/or may be grouped differently into event groups, as in the example depicted, than the subsequence patterns with which they are replaced.

Figure 5:
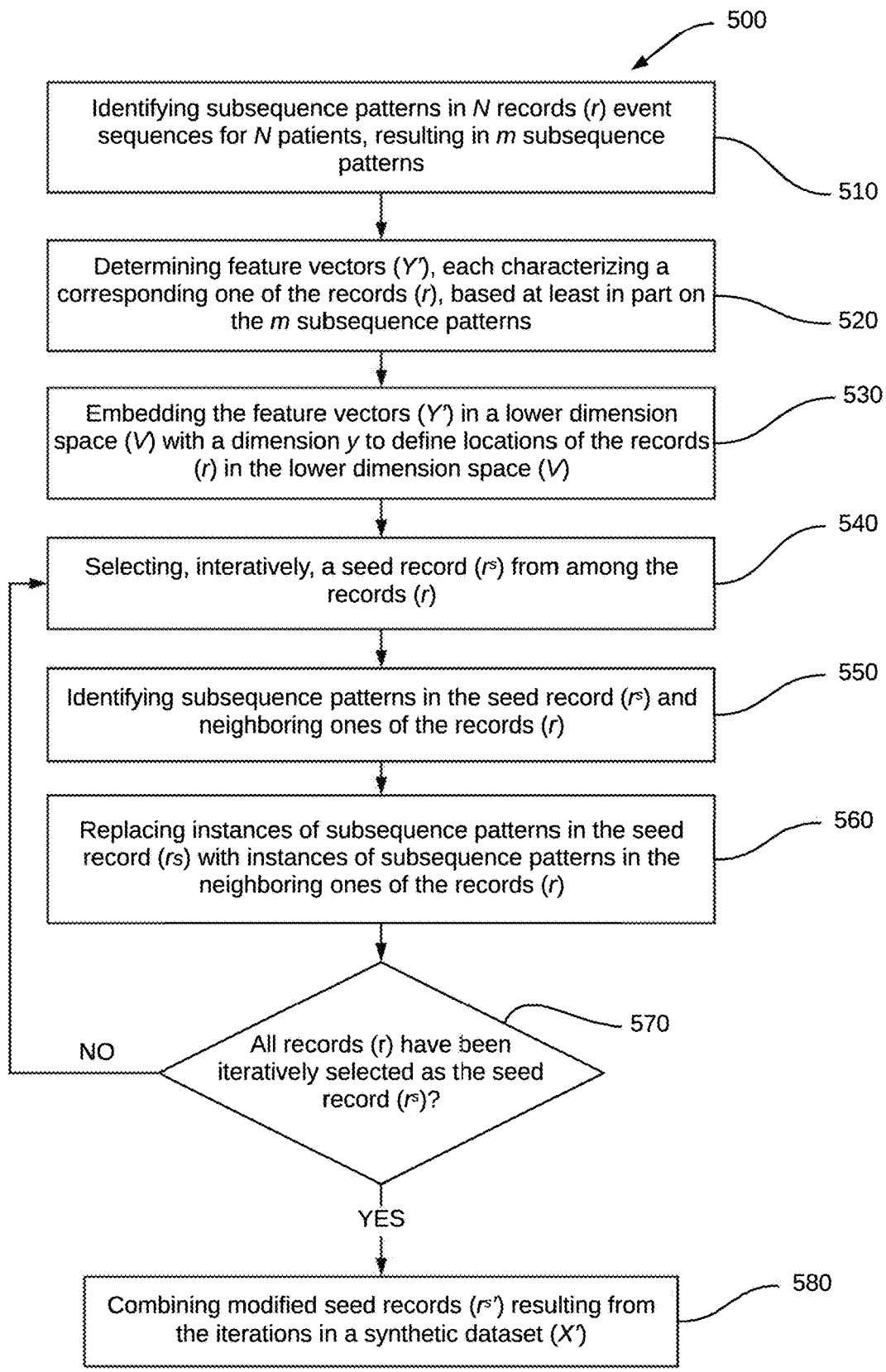
FIG. 5 is flowchart of a method for generating a synthetic longitudinal dataset.

FIG. 5 is flowchart of a method 500 for generating a synthetic longitudinal dataset (X'). The method includes identifying subsequence patterns in N records (r) defining event sequences for N patients, resulting in m subsequence patterns, where m and N are integers (510). Feature vectors (Y'), each characterizing a corresponding one of the records (r), are determined based at least in part on the m subsequence patterns (520). The feature vectors (Y') are embedded in a lower dimension space (V) with a dimension y to define locations of the records (r) in the lower dimension space (V), where y is an integer and m>y>0 (530). A seed record ($r^s$) is iteratively selected from among the records (r) (540). In each iteration, subsequence patterns are identified in a subset of the records (r), the subset being determined based at least in part on the locations of the records (r) in the lower dimension space (V) (550). Instances of subsequence patterns in the seed record ($r^s$) are replaced with corresponding instances of subsequence patterns in the subset of the records (r), based at least in part on a determined distance between the respective instances of subsequence patterns, to form a modified seed record ($r^{s'}$) (560). A determination is made as to whether all of the records (r) have been iteratively selected as the seed record ($r^s$) (570). If not, then the selecting of a seed record ($r^s$), the identifying of subsequence patterns, and the replacing of instances of subsequences in the seed record ($r^{s'}$) are iteratively repeated. If all of the records (r) have been iteratively selected as the seed record ($r^s$), then the modified seed records ($r^{s'}$) resulting from the iterations are combined in a synthetic dataset (X') (580).

In addition to the description above and accompanying figures, implementations may be based at least in part on the following methodological pseudo code for synthesizing longitudinal data from clinical trials:

1. Original dataset X; X is comprised of tables where each table consists of records of events, start and optional end dates as well as other categorical and numerical attributes for N patients
2. Concatenate the tables into dataset Y such that each row has subject ID, event code, event start and optionally event end date and other categorical and numerical values
3. Compute the conditional probability for observing event code a given event code b has occurred in a patient's timeline of events
4. Create a sequence of events per patient (total of N) ordered by the start date of the events
5. Use pattern mining to identify m frequent subsequence patterns across event sequences to be used as feature vectors Y'
6. Embed Y' into space V with dimension y (e.g. t-SNE, UMAP, PCA) producing embedded points (i.e. records)
7. Use the following properties:
   a. N>0 (size of the synthetic dataset)
   b. k>0 (number of neighbors also called cluster)
   c. y (embedding dimension m>y>0)
   d. c>=1, C⊆R
   e. p>=0, p⊆R
   f. T(·) transformation mechanism
8. Generate synthetic dataset X' with longitudinal data for N patients
   a. While i<=N do:
      i. Generate seed record $r^s$
      ii. Select k nearest neighbors of $r^s$
      iii. Generate new record $r^{s'}$ by
         1. Drop events e in event sequence for $r^s$ where the number of subjects event e is present is lower than count c
         2. Swap patterns of events across seed record $r^s$ and its k neighbors using pattern mining to identify patterns in $r^s$ and its k neighbors, finding instances of the patterns that are close to each other using a distance, and making swaps
         3. Finding all consecutive events where the conditional probability of event a occurring after event b is lower than p in the sequence from (2) and flipping the order of occurrence at random
         4. Anonymizing the start date of the first event in the event sequence of $r^s$ by adding noise sampled from a uniform distribution [−U, U]
         5. Adding noise to the lag between the first event and the starts and ends of all the following events such that the order of the sequence is preserved. The noise is added using Gaussian noise N(0, σ) however an alternate mechanism can be used
      iv. Store $r^{s'}$ for combining with other generated records to form X'
      v. i=i+1;
   b. end while To evaluate the fidelity of the synthesized longitudinal datasets, cross-validation tests were performed to compare properties of the synthetic datasets to properties of the real datasets to assess how well the underlying properties of the real datasets were preserved. As discussed in further detail below, a number of metrics can be used in the cross-validation, such as event sequence length, mean event duration, and event frequency. Another metric, not depicted in the plots discussed below, is the mean parameter value of continuous attributes for a specific event, such as measured heart rate. These mean values can be compared between the real data and the synthesized data, as discussed below. For categorical attributes (e.g., Ethnicity, Race, and Sex), mode and frequencies may be used as cross-validation measurements.

Figure 6A:
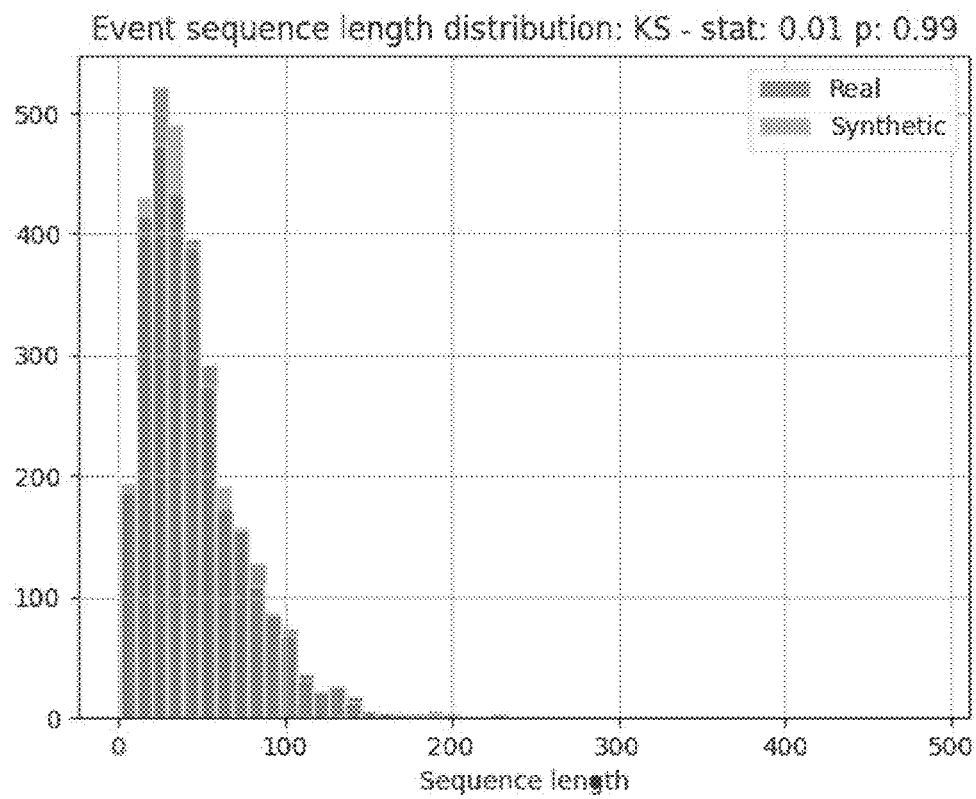
FIGS. 6A-6C are histograms of event sequence lengths for real and synthetic datasets for clinical trials directed to Non-Small Cell Lung Cancer (NSCLC), Acute Lymphoblastic Leukemia (ALL), and Multiple Myeloma, respectively.
Figure 6B:
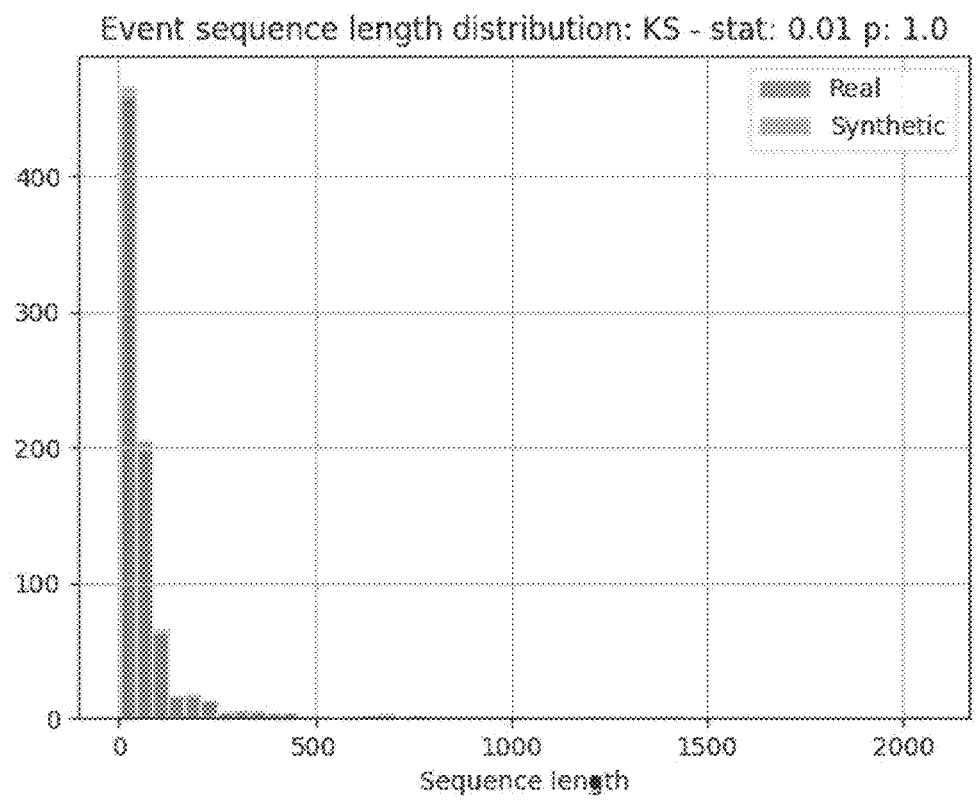
Figure 6C:
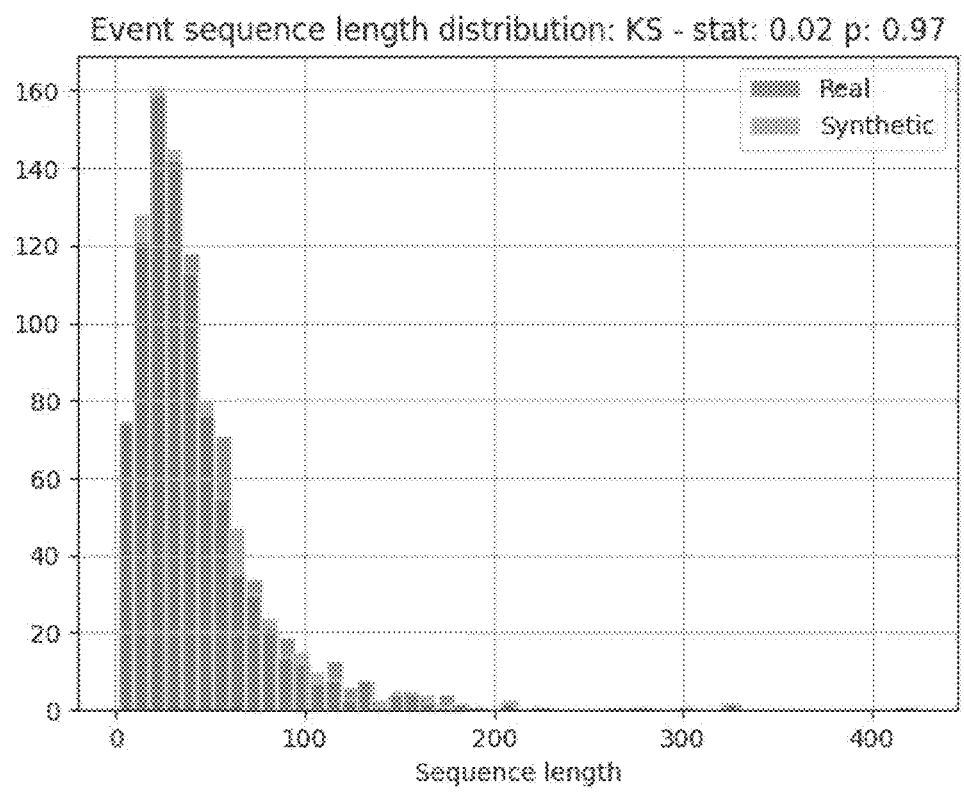

FIGS. 6A-6C are histograms of event sequence lengths for cross-validation of real and synthetic datasets for clinical trials directed to Non-Small Cell Lung Cancer (NSCLC), Acute Lymphoblastic Leukemia (ALL), and Multiple Myeloma, respectively. The histograms show the lengths of records (r) defining event sequences from an original dataset (or "real dataset") overlaid on the lengths of records in a synthetic dataset produced according to the approaches described herein. The histograms may be compared statistically using, e.g., the Kolmogorov-Smirnov test, which can be used to compare a sample with a reference probability distribution. The Kolmogorov-Smirnov statistic quantifies a distance between the empirical distribution function of a sample (e.g., the synthetic dataset) and the cumulative distribution function of the reference distribution (e.g., the real dataset). The values of the Kolmogorov-Smirnov statistic for FIGS. 6A-6C are 0.01, 0.01, and 0.02, respectively, where the value approaches zero as the difference between the distributions decreases. The Kolmogorov-Smirnov test produces a measure of goodness-of-fit, with values of p=0.99, p=1.0, and p=0.97, respectively, where p=1.0 indicates a perfect fit.

FIGS. 7A-7F are plots of cross-validation test results for clinical trials directed to NSCLC. FIGS. 8A-8F are plots of cross-validation test results for clinical trials directed to ALL. FIGS. 9A-9F are plots of cross-validation test results for clinical trials relating to Multiple Myeloma.

Figure 7A:
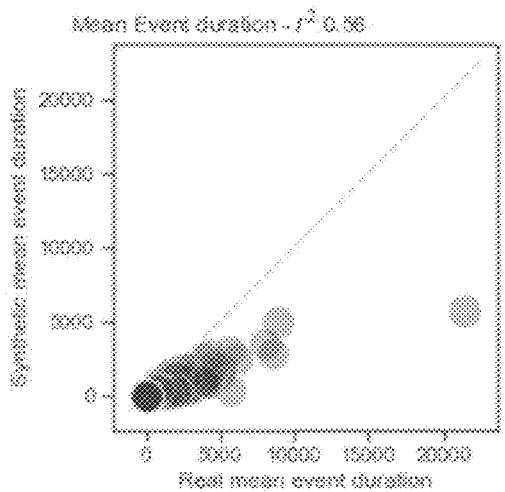
FIGS. 7A-7F are plots of cross-validation test results for clinical trials directed to NSCLC.
Figure 8A:
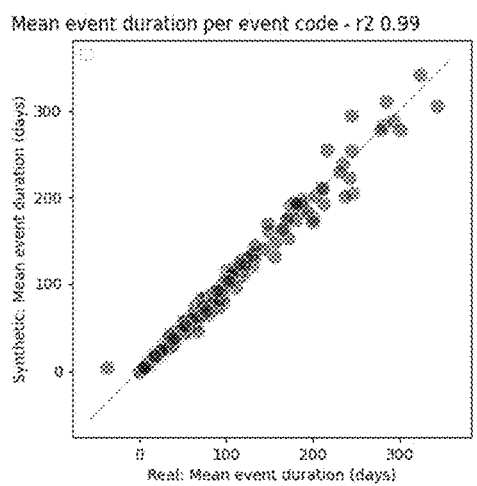
FIGS. 8A-8F are plots of cross-validation test results for clinical trials directed to ALL.
Figure 9A:
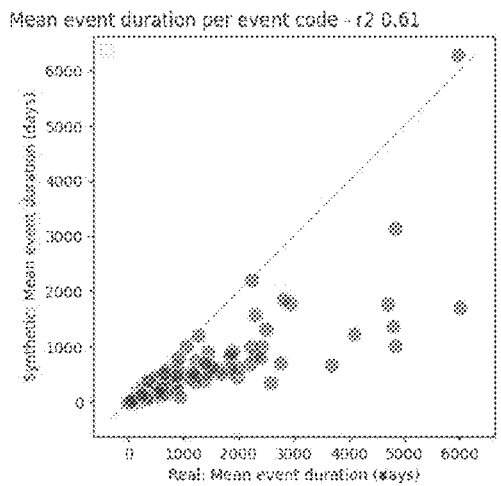
FIGS. 9A-9F are plots of cross-validation test results for clinical trials relating to Multiple Myeloma.

FIGS. 7A, 8A, and 9A show a comparison of mean duration of events between a real dataset and a synthetic dataset, for events having both a start date (or date and time) and an end date (or date and time). For example, the mean duration of an adverse event, such as nausea, can be computed for the subjects in the synthetic dataset and compared with that of the real dataset. In these plots, data from the real dataset is plotted on the x-axis and data from the synthetic dataset is plotted on the y-axis. Therefore, an ideal distribution would be along a line having a slope of 1.0, as shown in the figures. The fit of the data to the ideal characteristic can be assessed using a simple linear regression and quantified using the coefficient of determination ($r^2$). The values of $r^2$ for FIGS. 7A, 8A, and 9A are 0.56, 0.99, and 0.61, respectively, where the value $r^2$=1.00 indicates a perfect fit to the linear characteristic.

Figure 7B:
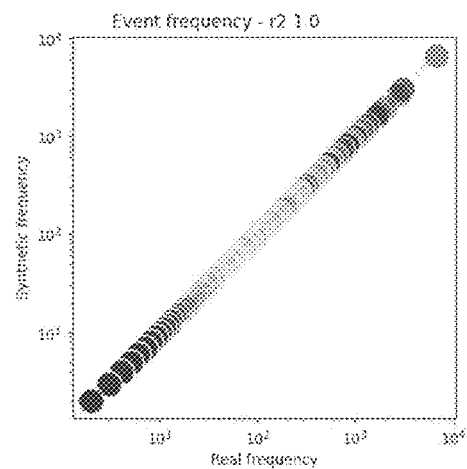
Figure 8B:
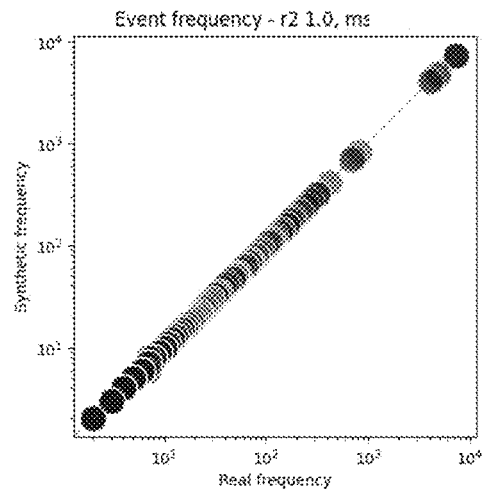
Figure 9B:
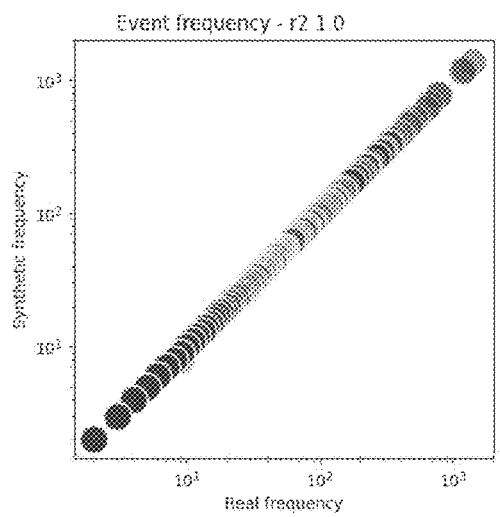

FIGS. 7B, 8B, and 9B show a comparison of event frequencies. In this example, the frequencies of all events, including, e.g., nausea, headache, or other symptoms, adverse events, blood pressure measurements, etc., are cumulatively determined. Data from the real dataset is plotted on the x-axis and data from the synthetic dataset is plotted on the y-axis, with both axes having a logarithmic scale in this example. An ideal distribution would be along a line having a slope of 1.0, as shown in the figures. The values of $r^2$ for FIGS. 7B, 8B, and 9B are 1.0, 1.0, and 1.0, respectively, where the value $r^2$=1.00 indicates a perfect fit to the linear characteristic.

Figure 7C:
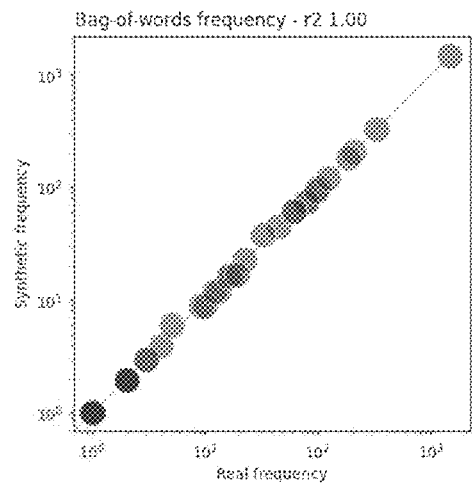
Figure 8C:
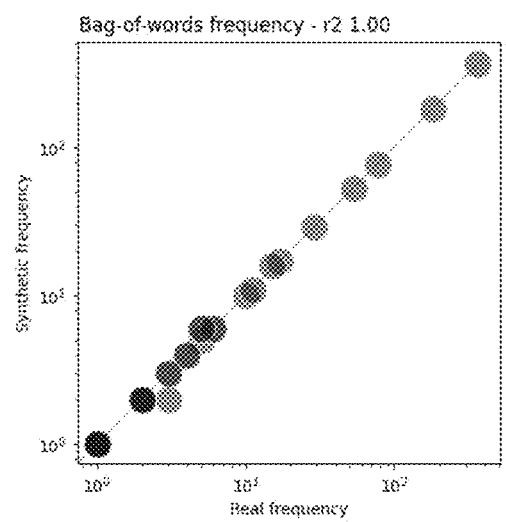
Figure 9C:
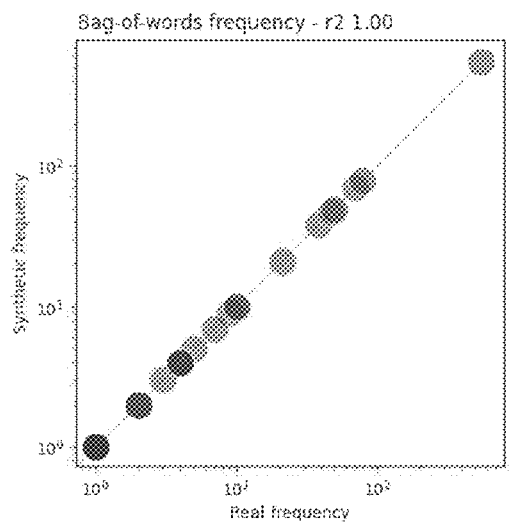

FIGS. 7C, 8C, and 9C show a comparison of "bag of words" (BoW) for event frequencies feature vectors between a real dataset and a synthetic dataset. In this example, the number of occurrences of each particular event, e.g., nausea, headache, or other symptoms, adverse events, blood pressure measurements, etc., is determined. Data from the real dataset is plotted on the x-axis and data from the synthetic dataset is plotted on the y-axis, with both axes having a logarithmic scale in this example. An ideal distribution would be along a line having a slope of 1.0, as shown in the figures. The values of $r^2$ for FIGS. 7C, 8C, and 9C are 1.0, 1.0, and 1.0, respectively, where the value $r^2$=1.00 indicates a perfect fit to the linear characteristic.

Figure 7D:
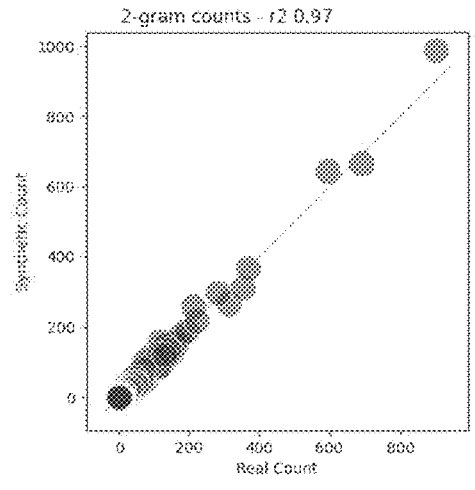
Figure 8D:
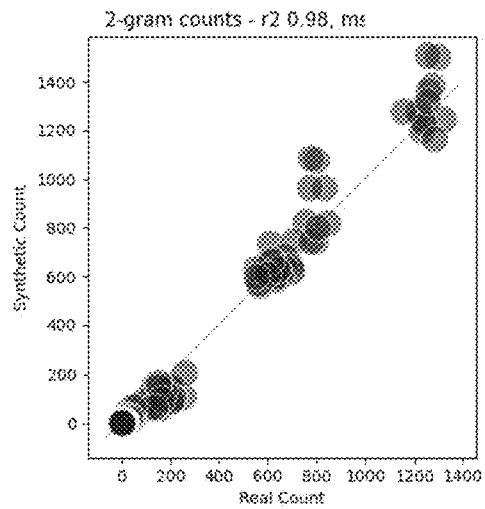
Figure 9D:
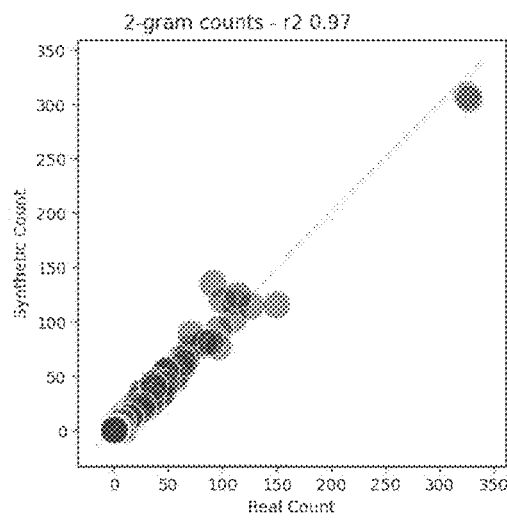

FIGS. 7D, 8D, and 9D show a comparison of a number of 2-gram counts between a real dataset and a synthetic dataset. The term "2-gram," in a usage akin to natural language processing, refers to sequences of two consecutive events. In this example, the number of occurrences of each particular event "2-gram" is determined. Data from the real dataset is plotted on the x-axis and data from the synthetic dataset is plotted on the y-axis. An ideal distribution would be along a line having a slope of 1.0, as shown in the figures. The values of $r^2$ for FIGS. 7D, 8D, and 9D are 0.97, 0.98, and 0.97, respectively, where the value $r^2$=1.00 indicates a perfect fit to the linear characteristic.

Figure 7E:
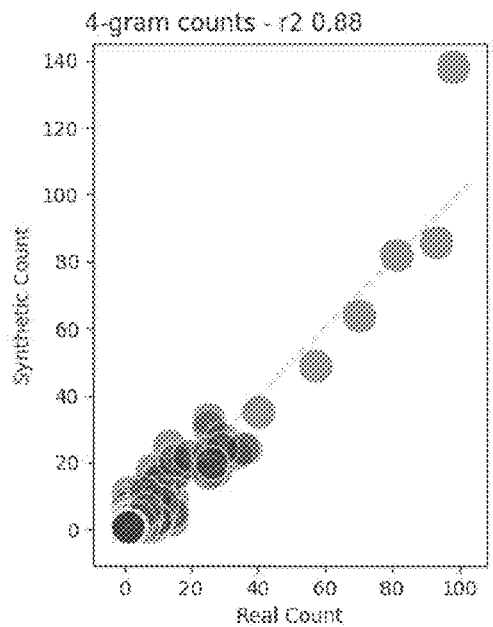
Figure 8E:
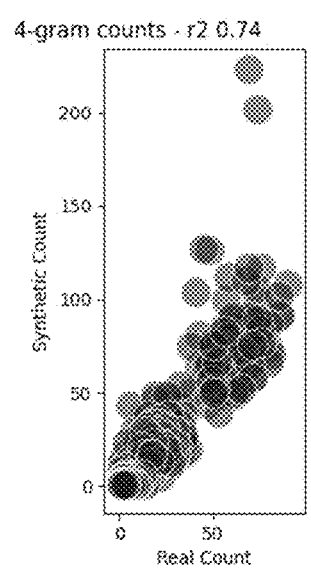
Figure 9E:
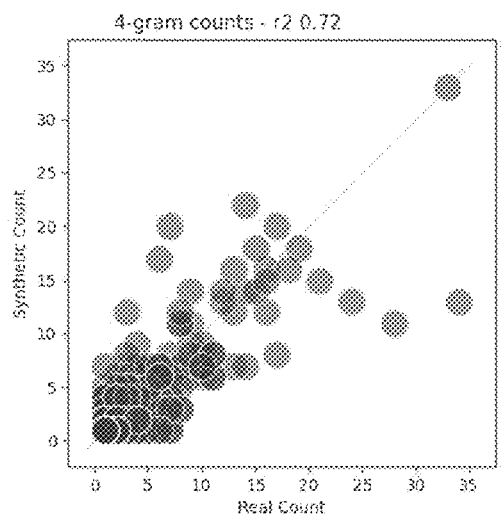

FIGS. 7E, 8E, and 9E show a comparison of a number of 4-gram counts between a real dataset and a synthetic dataset. The term "4-gram," in a usage akin to natural language processing, refers to sequences of four consecutive events (i.e., four events in a specific order). In this example, the number of occurrences of each particular event "4-gram" is determined. Data from the real dataset is plotted on the x-axis and data from the synthetic dataset is plotted on the y-axis. An ideal distribution would be along a line having a slope of 1.0, as shown in the figures. The values of $r^2$ for FIGS. 7E, 8E, and 9E are 0.88, 0.74, and 0.72, respectively, where the value $r^2$=1.00 indicates a perfect fit to the linear characteristic.

Figure 7F:
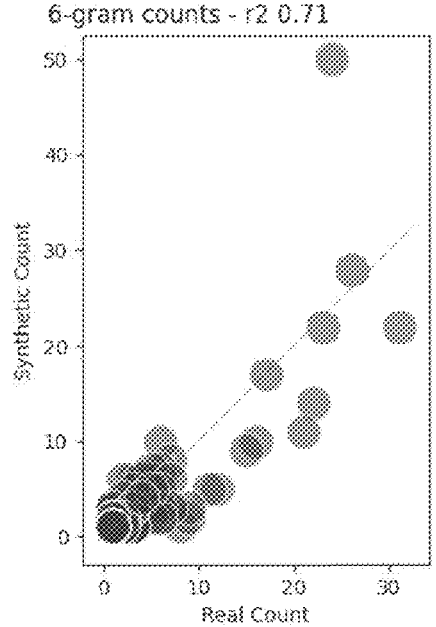
Figure 8F:
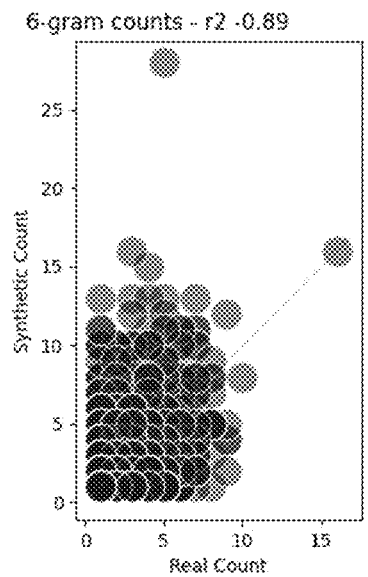
Figure 9F:
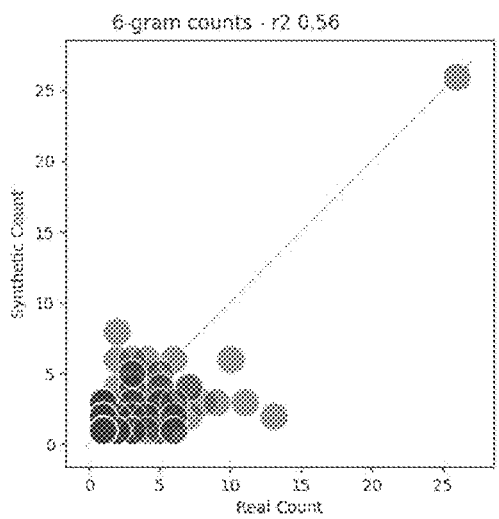
Figure 10A:
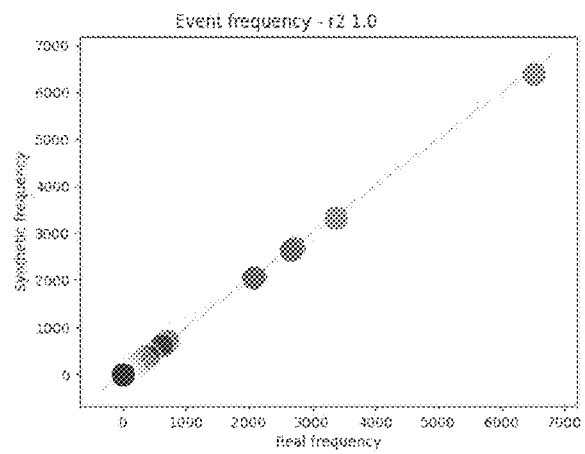
FIGS. 10A-10E are plots showing a comparison of real datasets to synthetic datasets to illustrate the performance of the disclosed method.
Figure 10B:
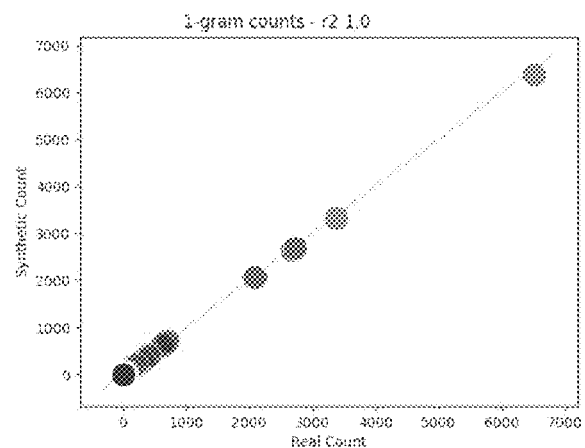
Figure 10C:
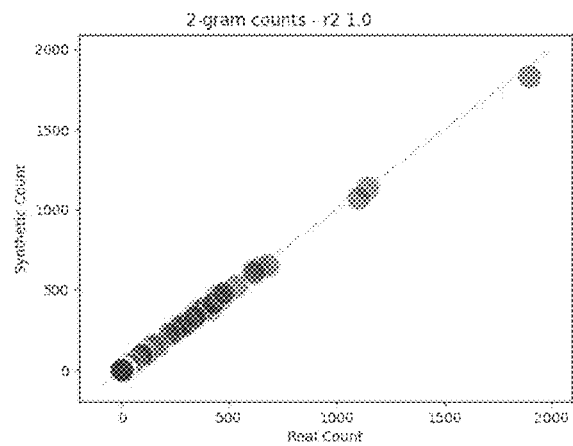
Figure 10D:
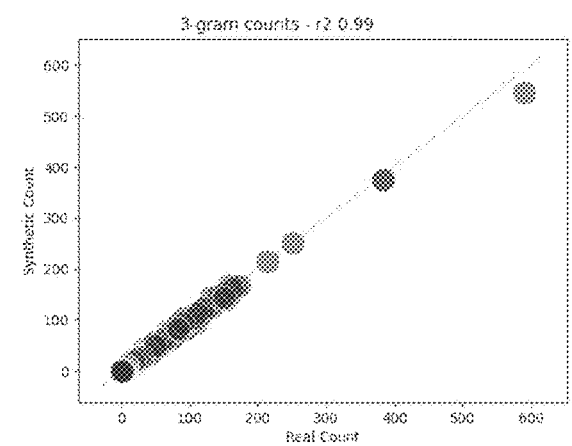
Figure 10E:
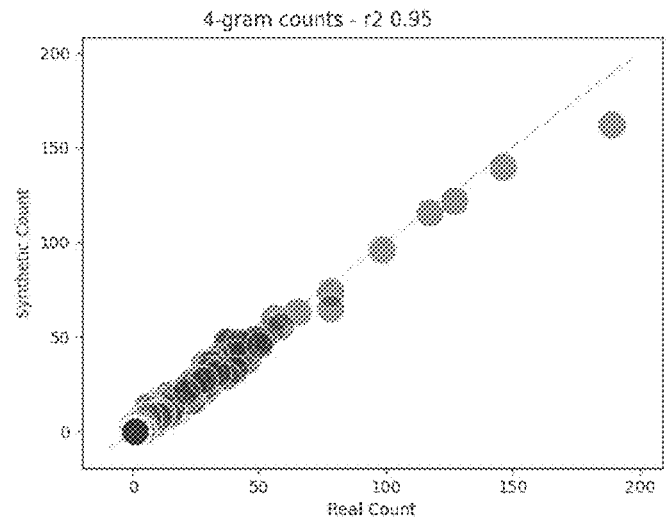
Figure 11A:
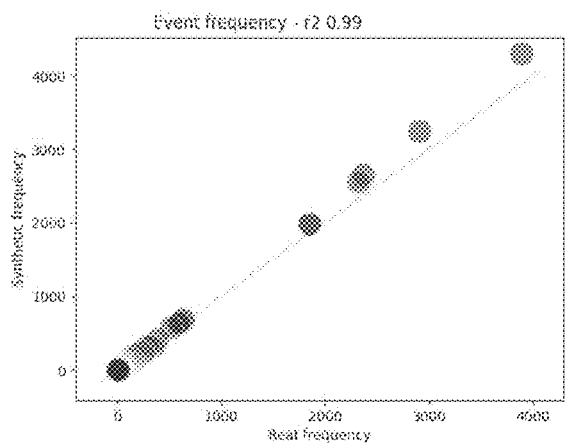
FIGS. 11A-11E are plots showing a comparison of real datasets to synthetic datasets to illustrate the performance of the n-gram model used in Natural Language Processing (NLP).
Figure 11B:
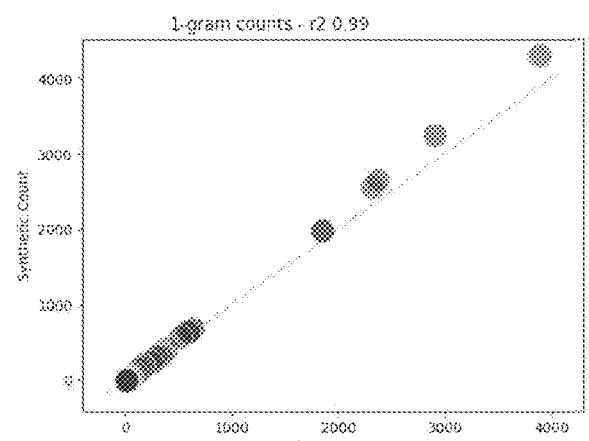
Figure 11C:
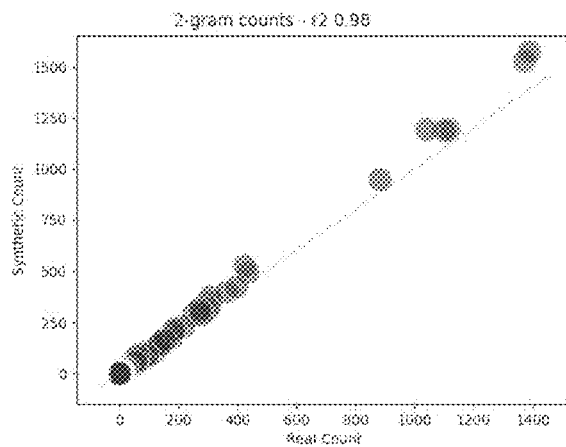
Figure 11D:
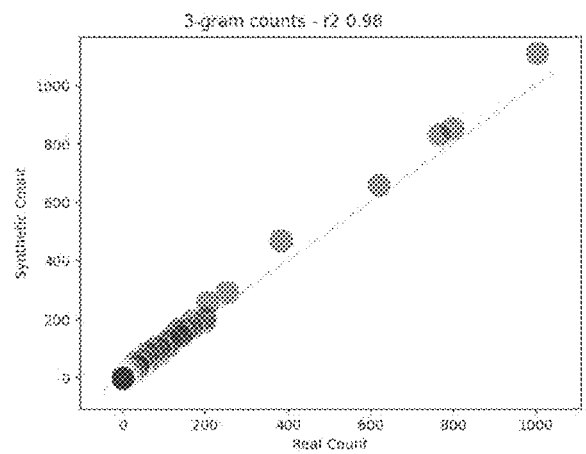
Figure 11E:
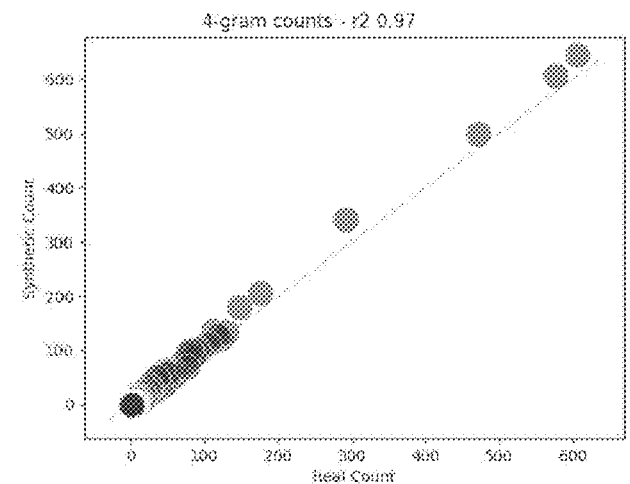
Figure 12A:
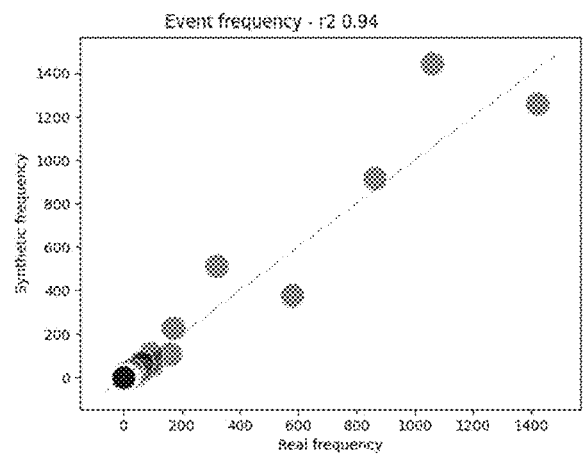
FIGS. 12A-12E are plots showing a comparison of real datasets to synthetic datasets to illustrate the performance of a Long Short-Term Memory (LSTM) neural network.
Figure 12B:
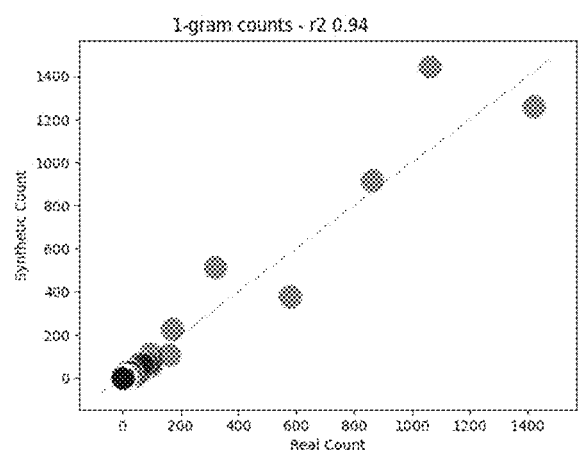
Figure 12C:
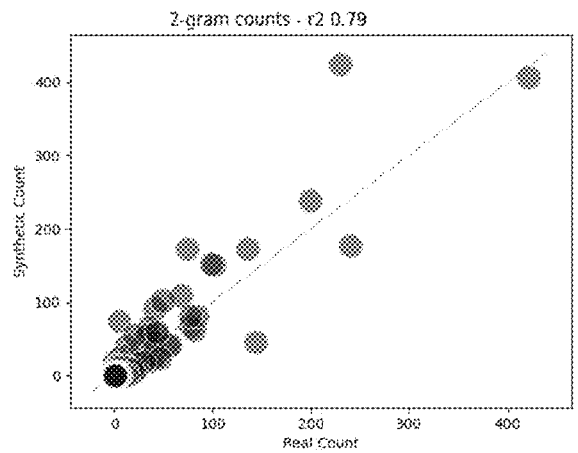
Figure 12D:
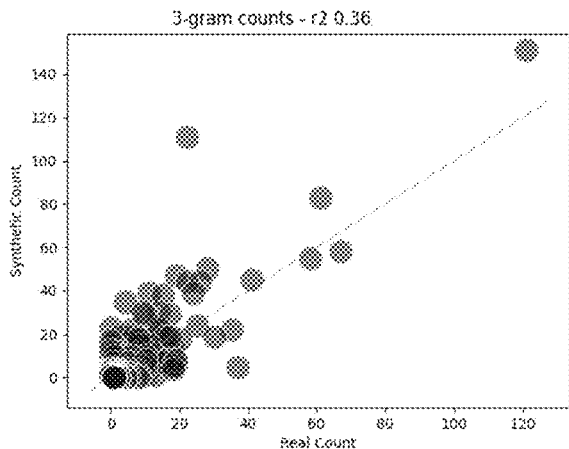
Figure 12E:
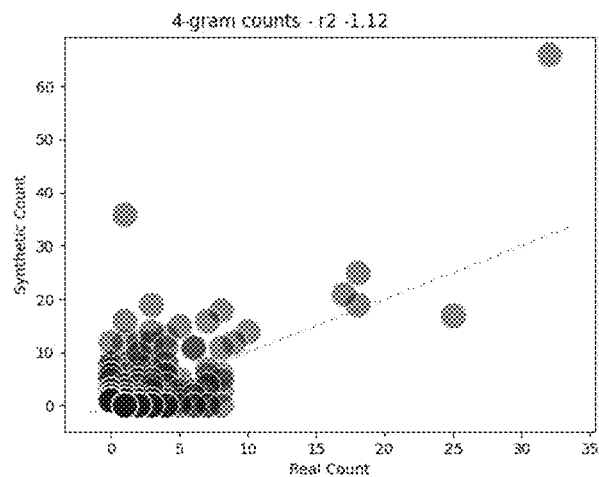
Figure 13A:
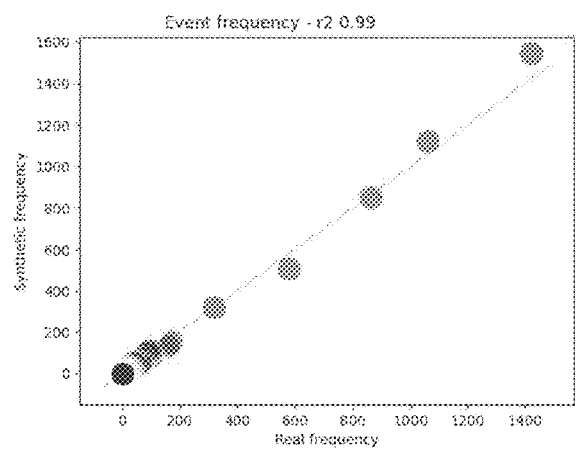
FIGS. 13A-13E are plots showing a comparison of real datasets to synthetic datasets to illustrate the performance of a Convolutional Neural Network (CNN).
Figure 13B:
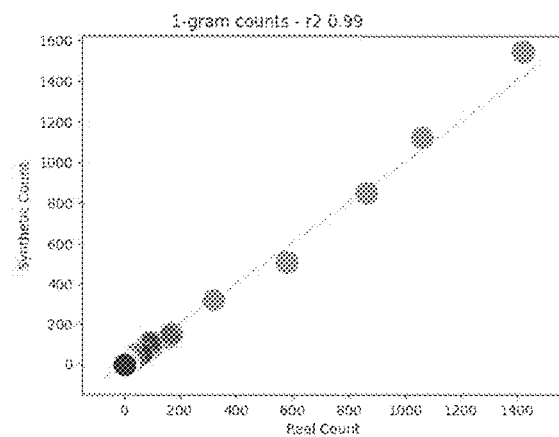
Figure 13C:
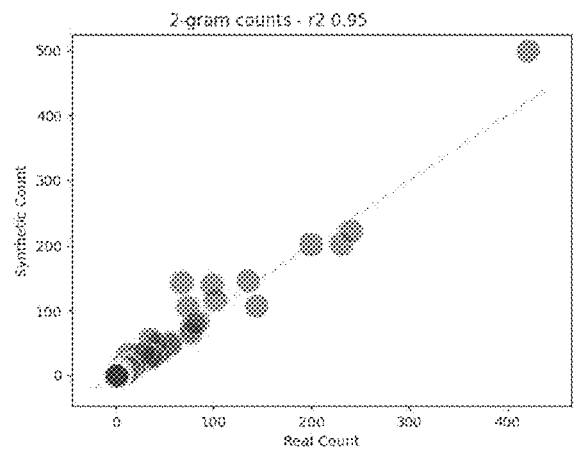
Figure 13D:
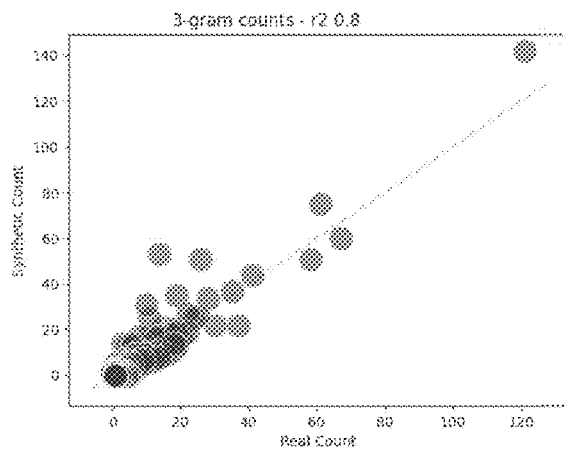
Figure 13E:
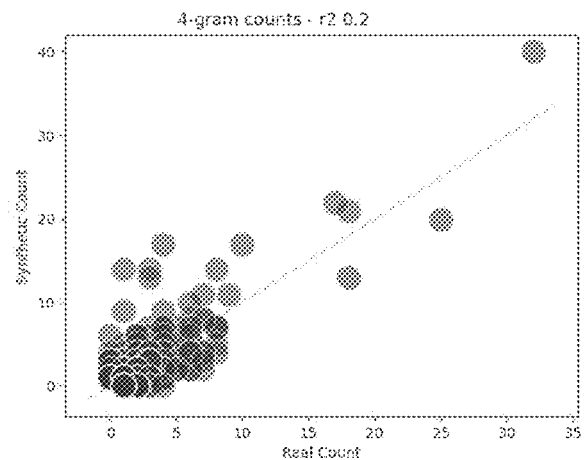

FIGS. 7F, 8F, and 9F show a comparison of a number of 6-gram counts between a real dataset and a synthetic dataset. The term "6-gram," in a usage akin to natural language processing, refers to sequences of six consecutive events (i.e., six events in a specific order). In this example, the number of occurrences of each particular event "6-gram" is determined. Data from the real dataset is plotted on the x-axis and data from the synthetic dataset is plotted on the y-axis. An ideal distribution would be along a line having a slope of 1.0, as shown in the figures. The values of $r^2$ for FIGS. 7F, 8F, and 9F are 0.71, 0.89, and 0.56, respectively, where the value $r^2$=1.00 indicates a perfect fit to the linear characteristic.

FIGS. 10A-10E, 11A-11E, 12A-12E, and 13A-13E are plots showing performance comparisons of the disclosed method (FIGS. 10A-10E) with other techniques including non-neural network methods such as the n-gram model used in Natural Language Processing (NLP) (FIGS. 11A-11E) and neural network approaches, such as Long Short-Term Memory (LSTM) (FIGS. 12A-12E) and Convolutional Neural Network (CNN) (FIGS. 13A-13E).

FIGS. 10A-10E are plots showing a comparison of real (i.e., original) datasets to synthetic datasets to illustrate the performance of the disclosed method, including, respectively, event frequencies, 1-gram, 2-gram, 3-gram, and 4-gram, where the term "n-gram," in a usage akin to natural language processing, refers to sequences of n consecutive events (or single events in the case of 1-gram).

FIGS. 11A-11E are plots showing a comparison of real datasets to synthetic datasets to illustrate the performance of the n-gram model used in Natural Language Processing (NLP), including, respectively, event frequencies, 1-gram, 2-gram, 3-gram, and 4-gram.

FIGS. 12A-12E are plots showing a comparison of real datasets to synthetic datasets to illustrate the performance of a Long Short-Term Memory (LSTM) neural network, including, respectively, event frequencies, 1-gram, 2-gram, 3-gram, and 4-gram.

FIGS. 13A-13E are plots showing a comparison of real datasets to synthetic datasets to illustrate the performance of a Convolutional Neural Network (CNN), including, respectively, event frequencies, 1-gram, 2-gram, 3-gram, and 4-gram.

Figure 14A:
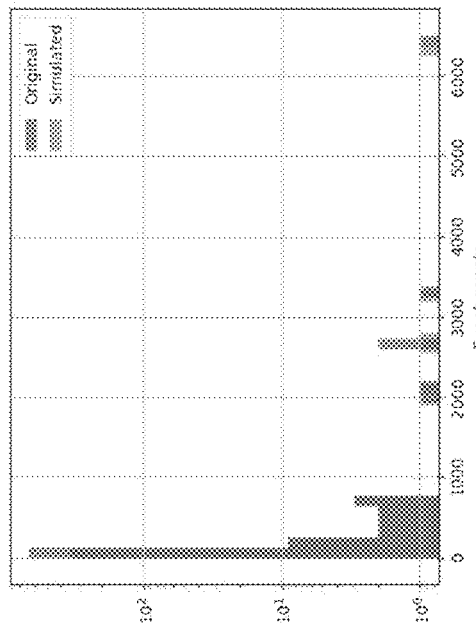
FIGS. 14A-14H are plots showing a comparison of real datasets to synthetic datasets to illustrate the performance the techniques discussed herein with respect to event sequence length and event type frequency.
Figure 14B:
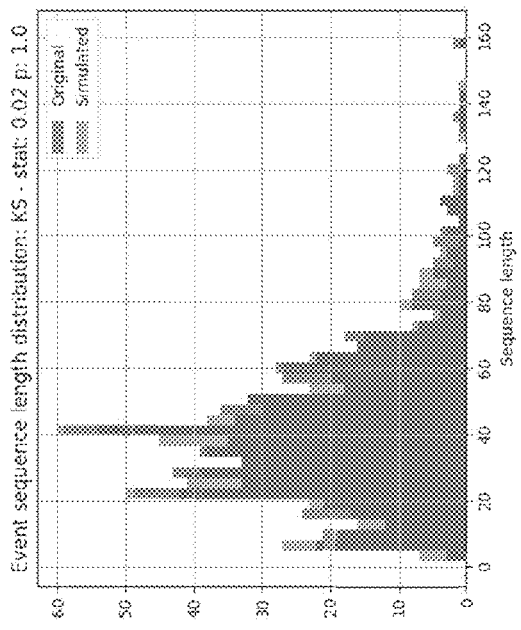
Figure 14C:
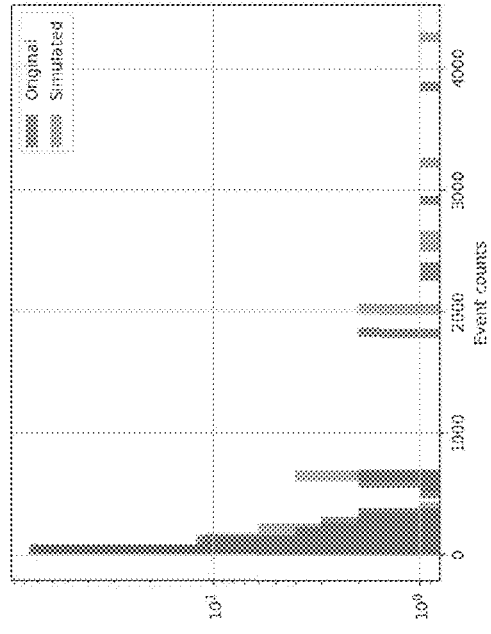
Figure 14D:
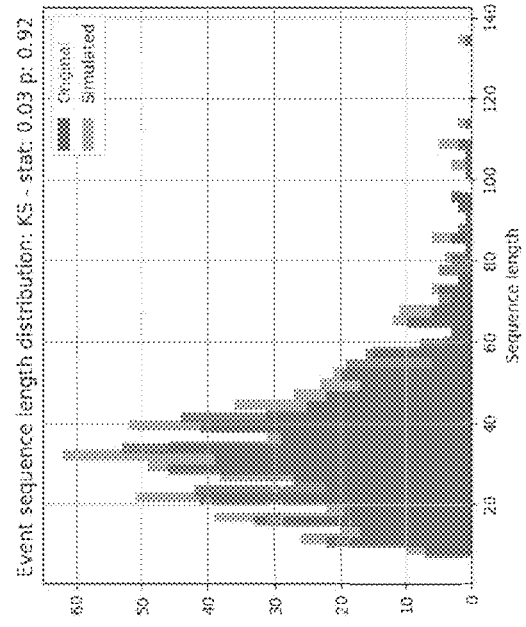
Figure 14E:
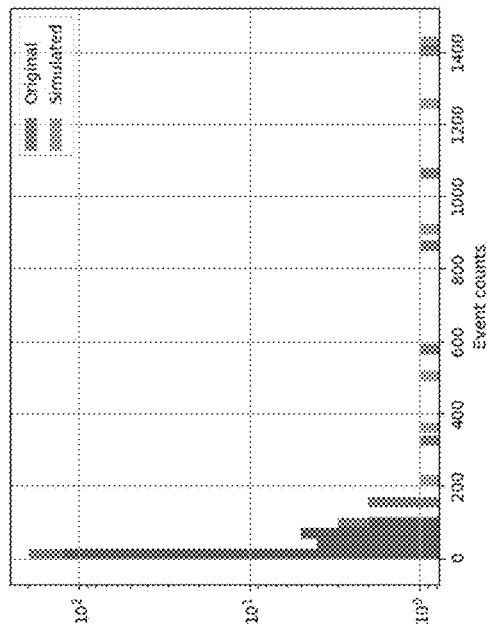
Figure 14F:
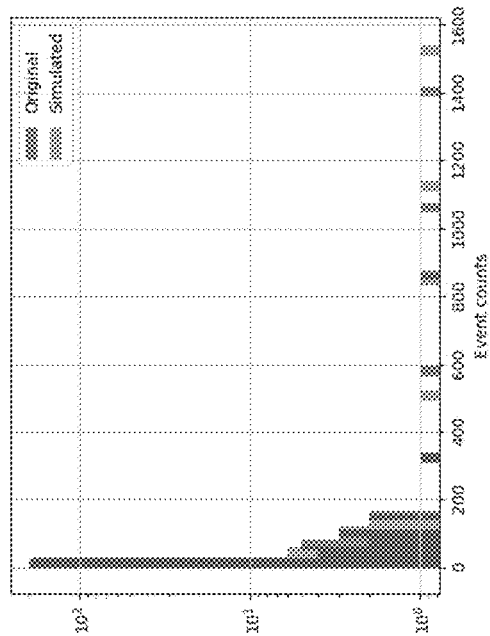
Figure 14G:
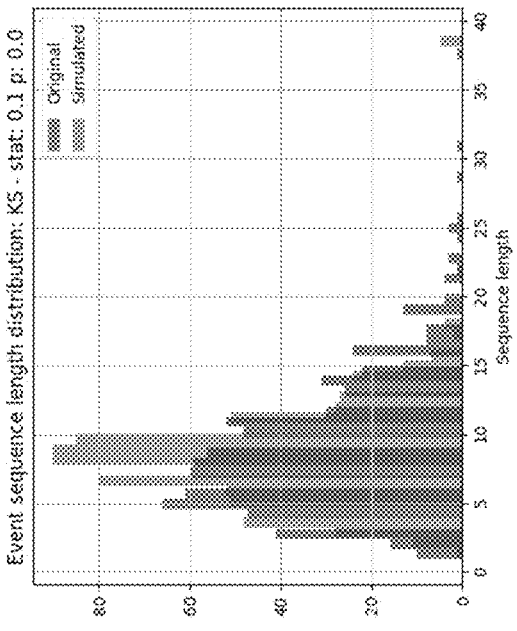
Figure 14H:
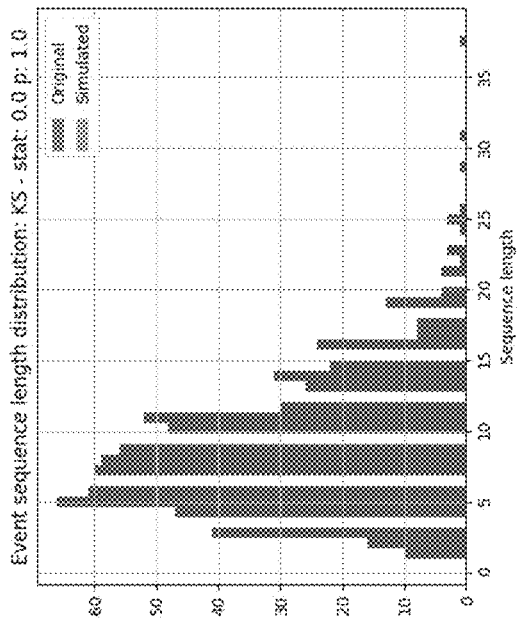

FIGS. 14A-14H are plots showing a comparison of real datasets to synthetic datasets to illustrate the performance the techniques discussed above with respect to event sequence length (FIGS. 14A, 14C, 14E, and 14G) and event type frequency (FIGS. 14B, 14D, 14F, 14H). The plots compare the performance the disclosed method (FIGS. 14A-14B) with other techniques including non-neural network methods such as the n-gram model used in Natural Language Processing (NLP) (FIGS. 14C-14D) and neural network approaches, such as Long Short-Term Memory (LSTM) (FIGS. 14E-14F) and Convolutional Neural Network (CNN) (FIGS. 14G-14H).

Aspects of the present invention may be embodied in the form of a system, a computer program product, or a method. Similarly, aspects of the present invention may be embodied as hardware, software, or a combination of both. Aspects of the present invention may be embodied as a computer program product saved on one or more computer-readable media in the form of computer-readable program code embodied thereon.

The computer-readable medium may be a computer-readable storage medium. A computer-readable storage medium may be, for example, an electronic, optical, magnetic, electromagnetic, infrared, or semiconductor system, apparatus, or device, or any combination thereof.

Computer program code in embodiments of the present invention may be written in any suitable programming language. The program code may execute on a single computer, or on a plurality of computers. The computer may include a processing unit in communication with a computer-usable medium, where the computer-usable medium contains a set of instructions, and where the processing unit is designed to carry out the set of instructions.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A method for generating a synthetic longitudinal dataset (X'), the method comprising:
    identifying subsequence patterns in N records (r) defining event sequences for N patients, resulting in m subsequence patterns, where m and N are integers;
    determining feature vectors (Y'), each characterizing a corresponding one of the records (r), based at least in part on said m subsequence patterns;
    embedding the feature vectors (Y') in a lower dimension space (V) with a dimension y to define locations of the records (r) in the lower dimension space (V), where y is an integer and m>y>0;
    selecting, iteratively, a seed record ($r^s$) from among the records (r), and in each iteration:
        identifying subsequence patterns in a subset of the records (r), the subset being determined based at least in part on the locations of the records (r) in the lower dimension space (V);
        replacing one or more instances of subsequence patterns in the seed record ($r^s$) with instances of corresponding subsequence patterns identified in the subset of the records (r), based at least in part on a determined distance between the respective instances of subsequence patterns, to form a modified seed record ($r^{s'}$); and
    repeating said selecting, said identifying, and said replacing until all of the records (r) have been iteratively selected as the seed record ($r^s$); and
    combining modified seed records ($r^{s'}$) resulting from the iterations in a synthetic dataset (X').

2. The method of claim 1, wherein a dataset (Y) comprises event records for said N patients, each event record including a patient identifier, a start date of an event, or a start date of the event and an end date of the event, and one or more attributes of the event, the method further comprising:
    determining, for each of said N patients, an event sequence ordered by the start date of each event of the event records associated with each respective one of said N patients to produce said N records (r) defining event sequences for N patients.

3. The method of claim 2, wherein an original dataset (X) comprises a plurality of tables, each table comprising a subset of the event records for said N patients, the method further comprising concatenating said tables to form said dataset (Y).

4. The method of claim 1, wherein said m subsequence patterns comprise subsequence patterns having a frequency of occurrence greater than a defined threshold.

5. The method of claim 1, wherein said m subsequence patterns comprise m subsequence patterns having the highest frequencies of occurrence, where m is a defined parameter.

6. The method of claim 1, wherein said feature vectors (Y') are equal in length.

7. The method of claim 1, wherein said feature vectors (Y') comprise: (i) frequencies of occurrence of said m subsequence patterns; or (ii) binary presence or absence encoding of said m subsequence patterns.

8. The method of claim 1, wherein said embedding is performed using one or more of: t-distributed stochastic neighbor embedding (t-SNE), uniform manifold approximation and projection (UMAP), and principal component analysis (PCA).

9. The method of claim 1, wherein the subset of records (r) corresponds to the k nearest neighbors of the seed record ($r^s$) in the lower dimension space (V), where k is an integer.

10. The method of claim 1, wherein said replacing is performed only for subsequence patterns for which the determined distance between the respective instances of subsequence patterns is less than a defined distance threshold.

11. The method of claim 1, wherein said replacing is performed by replacing said one or more instances of subsequence patterns in the seed record ($r^s$) with instances of corresponding subsequence patterns randomly selected from a group of subsequence patterns having respective distances less than a defined distance threshold.

12. The method of claim 1, wherein, in said replacing, subsequences for which a total number of occurrences in said N event sequences is less than a determined threshold are excluded.

13. The method of claim 1, further comprising, in each iteration, randomizing a start date of a first event in the seed record ($r^s$).

14. The method of claim 1, further comprising, in each iteration, randomizing a gap between one or more pairs of the events in the seed record ($r^s$).

15. The method of claim 1, further comprising:
    determining, in each of said N event sequences, a conditional probability for each event given that a preceding event has occurred; and
    randomly swapping, in each iteration, each event with a respective preceding event when said conditional probability is less than a defined threshold.

16. The method of claim 1, further comprising outputting the synthetic dataset (X') to a storage system providing encryption and access controls.

17. A system for generating a synthetic longitudinal dataset (X'), comprising:
    a computer having one or more processors in communication with a memory, the memory storing instructions executable by said one or more processors to perform:
        identifying subsequence patterns in N records (r) defining event sequences for N patients, resulting in m subsequence patterns, where m and N are integers;
        determining feature vectors (Y'), each characterizing a corresponding one of the records (r), based at least in part on said m subsequence patterns;

embedding the feature vectors (Y') in a lower dimension space (V) with a dimension y to define locations of the records (r) in the lower dimension space (V), where y is an integer and m>y>0;

selecting, iteratively, a seed record ($r^s$) from among the records (r), and in each iteration:

identifying subsequence patterns in a subset of the records (r), the subset being determined based at least in part on the locations of the records (r) in the lower dimension space (V);

replacing one or more instances of subsequence patterns in the seed record ($r^s$) with instances of corresponding subsequence patterns identified in the subset of the records (r), based at least in part on a determined distance between the respective instances of subsequence patterns, to form a modified seed record ($r^{s'}$); and repeating said selecting, said identifying, and said replacing until all of the records (r) have been iteratively selected as the seed record ($r^s$); and combining modified seed records ($r^{s'}$) resulting from the iterations in a synthetic dataset (X').

18. The system of claim 17, wherein a dataset (Y) comprises event records for said N patients, each event record including a patient identifier, a start date of an event, or a start date of the event and an end date of the event, and one or more attributes of the event, the memory further storing instructions executable by said one or more processors to perform:

determining, for each of said N patients, an event sequence ordered by the start date of each event of the event records associated with each respective one of said N patients to produce said N records (r) defining event sequences for N patients.

19. The system of claim 17, wherein said feature vectors (Y') comprise:
(i) frequencies of occurrence of said m subsequence patterns; or (ii) binary presence or absence encoding of said m subsequence patterns.

20. The system of claim 17, wherein the subset of records (r) corresponds to the k nearest neighbors of the seed record ($r^s$) in the lower dimension space (V), where k is an integer.

21. The system of claim 17, wherein the memory further stores instructions executable by said one or more processors to perform:

determining, in each of said N event sequences, a conditional probability for each event given that a preceding event has occurred; and randomly swapping, in each iteration, each event with a respective preceding event when said conditional probability is less than a defined threshold.

22. A non-transitory computer storage medium storing instructions that, when executed by one or more processors of a computer, cause said one or more processors to perform a method for generating a synthetic longitudinal dataset (X'), the method comprising:

identifying subsequence patterns in N records (r) defining event sequences for N patients, resulting in m subsequence patterns, where m and N are integers;

determining feature vectors (Y'), each characterizing a corresponding one of the records (r), based at least in part on said m subsequence patterns;

embedding the feature vectors (Y') in a lower dimension space (V) with a dimension y to define locations of the records (r) in the lower dimension space (V), where y is an integer and m>y>0;

selecting, iteratively, a seed record ($r^s$) from among the records (r), and in each iteration:

identifying subsequence patterns in a subset of the records (r), the subset being determined based at least in part on the locations of the records (r) in the lower dimension space (V);

replacing one or more instances of subsequence patterns in the seed record ($r^s$) with instances of corresponding subsequence patterns identified in the subset of the records (r), based at least in part on a determined distance between the respective instances of subsequence patterns, to form a modified seed record ($r^{s'}$); and repeating said selecting, said identifying, and said replacing until all of the records (r) have been iteratively selected as the seed record ($r^s$); and combining modified seed records ($r^{s'}$) resulting from the iterations in a synthetic dataset (X').

23. The computer storage medium of claim 22, wherein a dataset (Y) comprises event records for said N patients, each event record including a patient identifier, a start date of an event, or a start date of the event and an end date of the event, and one or more attributes of the event, the method further comprising:

determining, for each of said N patients, an event sequence ordered by the start date of each event of the event records associated with each respective one of said N patients to produce said N records (r) defining event sequences for N patients.

24. The computer storage medium of claim 22, wherein said feature vectors (Y') comprise: (i) frequencies of occurrence of said m subsequence patterns; or (ii) binary presence or absence encoding of said m subsequence patterns.

25. The computer storage medium of claim 22, wherein the subset of records (r) corresponds to the k nearest neighbors of the seed record ($r^s$) in the lower dimension space (V), where k is an integer.

26. The computer storage medium of claim 22, wherein the method further comprises:

determining, in each of said N event sequences, a conditional probability for each event given that a preceding event has occurred; and randomly swapping, in each iteration, each event with a respective preceding event when said conditional probability is less than a defined threshold.

* * * * *